US010258400B2

(12) United States Patent
Songer et al.

(10) Patent No.: US 10,258,400 B2
(45) Date of Patent: Apr. 16, 2019

(54) CABLE FIXATION DEVICE, INSTRUMENTS, AND METHODS

(71) Applicants: Matthew Songer, Marquette, MI (US); Francis Korhonen, Negaunee, MI (US); Jeffrey Mosteller, Skandia, MI (US); Wesley Leland Hanna, Marquette, MI (US); Branden Wainio, Negaunee, MI (US); Jeffrey Vlahos, Marquette, MI (US); Jason Sandstrom, Marquette, MI (US); Robert Kinney, Marquette, MI (US)

(72) Inventors: Matthew Songer, Marquette, MI (US); Francis Korhonen, Negaunee, MI (US); Jeffrey Mosteller, Skandia, MI (US); Wesley Leland Hanna, Marquette, MI (US); Branden Wainio, Negaunee, MI (US); Jeffrey Vlahos, Marquette, MI (US); Jason Sandstrom, Marquette, MI (US); Robert Kinney, Marquette, MI (US)

(73) Assignee: J. M. LONGYEAR MANUFACTURING LLC, Marquette, MI (US)

( * ) Notice: Subject to any disclaimer, the term of this patent is extended or adjusted under 35 U.S.C. 154(b) by 38 days.

(21) Appl. No.: 15/210,863

(22) Filed: Jul. 14, 2016

(65) Prior Publication Data

US 2017/0128114 A1    May 11, 2017

Related U.S. Application Data

(63) Continuation-in-part of application No. 14/216,913, filed on Mar. 17, 2014, now Pat. No. 9,439,698.

(Continued)

(51) Int. Cl.
*A61B 17/82* (2006.01)
*A61B 17/88* (2006.01)
*A61B 17/84* (2006.01)

(52) U.S. Cl.
CPC .......... *A61B 17/8861* (2013.01); *A61B 17/82* (2013.01); *A61B 17/842* (2013.01);
(Continued)

(58) Field of Classification Search
CPC ... A61B 17/82; A61B 17/842; A61B 17/8861; A61B 17/8869; A61B 17/8872; Y10T 24/398; Y10T 24/49
See application file for complete search history.

(56) References Cited

U.S. PATENT DOCUMENTS

| 3,952,377 | A | * | 4/1976 | Morell | .................. E04C 5/122 |
| | | | | | 24/136 R |
| 9,216,047 | B2 | * | 12/2015 | Bryant | ............... A61B 17/8869 |
| 9,439,698 | B2 | * | 9/2016 | Songer | ............... A61B 17/8894 |

* cited by examiner

*Primary Examiner* — Matthew J Lawson
(74) *Attorney, Agent, or Firm* — Device Patent LLC

(57) ABSTRACT

Various forms of a cable fixation device, instrumentation, kit, and methods useful for repairing the skeletal system are introduced. The system utilizes a clamp housing fixing a head end of a surgical cable therein. In an operative configuration the cable is looped around a damaged bone segment and reentered through a lock aperture in the clamp housing then through a multi-part collet and lock cap residing within a lock aperture. The cable loop and each aforementioned component comprise a central axis aligned within a single plane. A sliding interface situated between the lock cap and collet prevent twisting of the surgical cable. The locking mechanism is non-destructive to the cable despite repeated unlocking and relocking of the fixation (Continued)

device. The axis for tensioning of the cable is coincident with the locking axis. A cerclage inserter instrument is disclosed.

18 Claims, 20 Drawing Sheets

Related U.S. Application Data

(60) Provisional application No. 61/801,837, filed on Mar. 15, 2013, provisional application No. 62/192,301, filed on Jul. 14, 2015.

(52) U.S. Cl.
CPC ...... *A61B 17/8869* (2013.01); *A61B 17/8872* (2013.01); *A61B 17/8894* (2013.01); *Y10T 24/398* (2015.01); *Y10T 24/49* (2015.01)

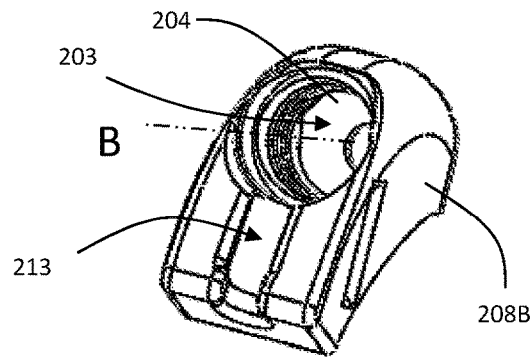
FIG. 10
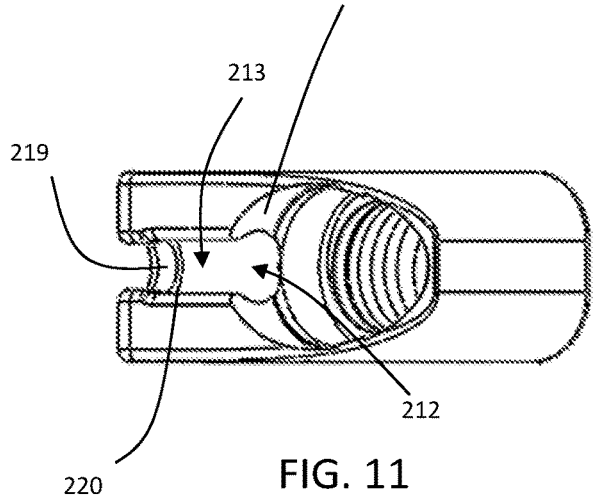
FIG. 11
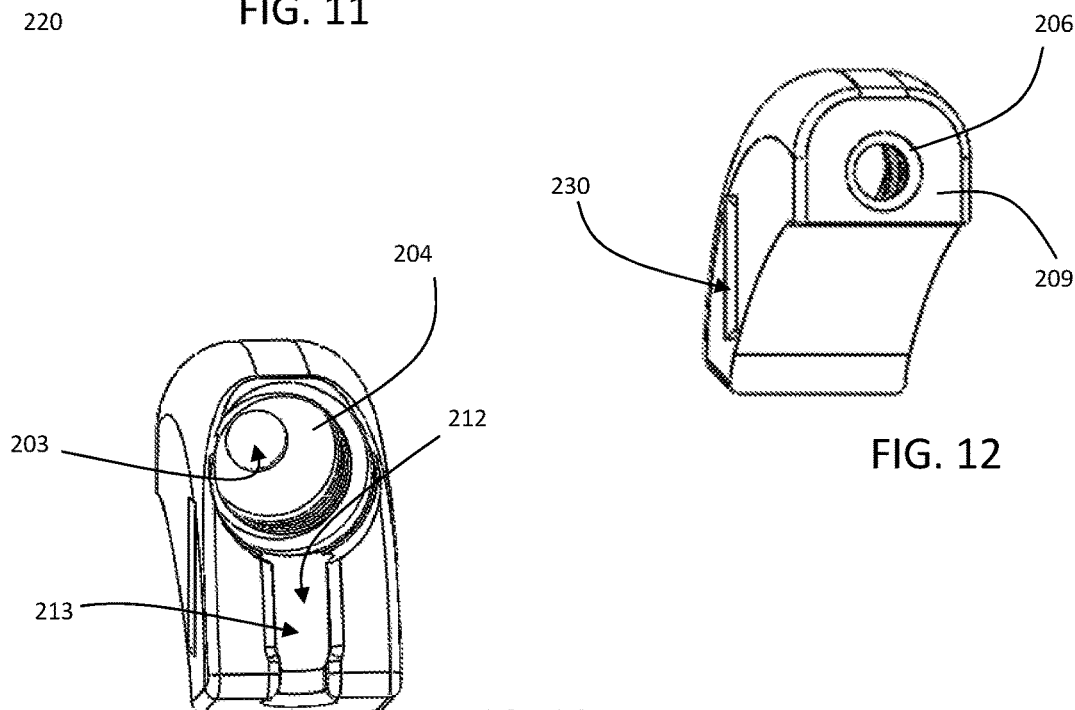
FIG. 12
FIG. 13

Axis-C

CABLE FIXATION DEVICE, INSTRUMENTS, AND METHODS

This application is a Continuation-In-Part application claiming priority to pending Non-Provisional patent application Ser. No. 14/216,913 filed on Mar. 17, 2014 which claims the benefit to now Provisional Patent Application No. 61/801,837 filed on Mar. 15, 2013. This application also claims priority to Provisional Patent Application No. 62/192,301 filed on Jul. 14, 2015. This application is also related to PCT Application No. WO2014145979, filed Mar. 17, 2014, pending European Application 14763374.7 filed Oct. 14, 2015, and pending Canadian Application No. 2,907,345 filed Sep. 15, 2015. The entire disclosure of each of these applications is hereby incorporated by reference and relied upon.

BACKGROUND OF THE INVENTION

Field of the Invention

The invention relates generally to surgical implants and instruments, and more particularly to surgical tensioning lines such as surgical cable, devices for fixation of surgical cable during surgery, and related instruments and methods.

Surgical cable is used by orthopedic surgeons in a variety of surgical applications but primarily for the stabilization of bone and bone segments. For example, in an open heart surgery procedure, the sternum is cut into two halves and each half is retracted to access the heart. Following the surgical repairs to the heart, the sternum is often rejoined using surgical cable looped around the two halves of the sternum, the loop is tensioned then fixated therein providing the stability required for the two halves of the bone to fuse.

Surgical cable may also be used to secure individual vertebral body segments to an elongated spinous rod for stabilization after spinal fracture or in an effort to correct a spinal deformity. Surgical cable is also effective at stabilizing fractures in long bones of the extremities such as in the femur. In these cases the cable is looped, also known as cerclaged, around the bone through a bone plate or a crimp, tightened to a specified tension with a tensioner tool, and then locked with a cable crimp or screw biting down on a crimp to clamp the cable.

Although effective in many cases, these methods can be improved. Commonly the cable tensioner and the screw that locks down on the crimp are separated by an angle thereby necessitating the operation of two spaced instruments at once in a small surgical space. Also, repairing a fracture may require sequentially tensioning several different cables at a provisional tension and then returning for a final tensioning. This method typically requires the use of a 'retensioner' instrument on each cable used at the front of a tensioning instrument to maintain tension in the cable while the tensioning instrument is moved to the cable to be tightened. This method, albeit cumbersome, eliminates the need to deform the crimp during a provisional step which may cause damage to the cable or crimp.

Description of Related Art

Surgical wires and cable has a history of use for the repair of the skeletal system. Their usefulness has suffered due to various deficiencies in their function.

For example, Kilpela et al. in U.S. Pat. No. 5,415,658 discloses a cable loop connector. When utilizing this connector, the instruments required to tension the cable and lock the cable are situated along two axis's more than 90 degrees apart. This excessively wide spread between instruments requires a larger incision and increases difficulty in handling. In addition, the locking portion of the connector utilizes an internal crimp making it unuseable for a plurality of locking and unlocking cycles when cable re-adjustments are needed.

Mattchen et al. in U.S. Pat. No. 7,207,090 discloses another form of cable retaining device for retaining flexible cables under tension. The device includes a body with an internal tapered void. A wedge shaped plug with recessed edges for containment of a cable is slidable into the void therein locking the cable between the body and plug. During clamping the slidable plug creates friction against the cable member potentially damaging the cable. Due to this, this system is also unsuitable for a plurality of locking and unlocking cycles.

Allen et al. discloses in U.S. Pat. No. 7,255,701 various forms of looped cable locking mechanisms. Most embodiments suffer from having each end of the cable loop spaced from each other along the long axis of the bone under repair. The cable within the loop fails to lay in the same plane therein causing a torsional force on the locking mechanism and improper seating on the bone. In addition, the disclosed embodiments have a tensioning axis that is not aligned with the locking axis causing difficulties using instrumentation within a small surgical access space.

Justin el al. discloses in U.S. Pat. No. 8,241,288 a collet fixation system for a cable loop and a cable locking instrument. In this bone fixation element, a cable passes through a pair of passageways in which the cable is secured. These passageways are separated by a space along the length of the bone therein once again imparting a torsional force on the fixation element as the cable is tensioned and causing it to not seat properly on the bone. An additional shortcoming is that the collet in this device is threaded. The collet will collapse down and bind the cable as the collet is advanced in rotation causing the cable to be twisted therein imparting unnecessary torsional forces on the cable that could lead to failure. An instrument is disclosed for advancing the collet while stabilizing the fixation element from rotation. Integrated within the C-shaped frame of the instrument is a handle of a collet driver co-aligned with the longitudinal axis of the collet. The positioning of the handle within the frame makes the drive handle both difficult to reach by hand and difficult to impart a hand torsional force. Also, the instrument utilizes a plurality of prongs (6) spaced in a radial pattern to interface with the fixation element. The quantity of prongs and their rounded profile is not well suited for firm control over the fixation element.

Several other cabling systems utilize crimps to lock the cable loop in a predetermined cable tension. These systems generally cannot be repeatedly 'unlocked' then 'relocked' when further adjustments by the surgeon need to be made.

What is needed are improved cerclage cable implants and corresponding instruments configured for eased insertion and robust performance. The needed improvements include a reduction of the number of instruments required to complete the surgical procedure, a reduction in the number of instruments used within the incision at the same time, and providing easy provisional cable locking and unlocking to provide the surgeon repeated cable adjustment without detrimental surgical consequences. It is also desirable that provisional cable locking and unlocking systems fully lock and unlock. In the unlocked position the cable must move freely without binding through the locking component providing for easy readjustment of tension and implant position. It is also desirable that the locking component on the cable applies generally uniform force across the cable to improve fixation while reducing the potential for cable damage. Also desirable are instruments that restrain implants to the instruments without fear of unintended fall off in the surgical corridor while providing prompt release of the implant at the completion of the surgical procedure.

SUMMARY OF THE INVENTION

Disclosed herein are improved implants, instruments, and methods of use of novel cable fixation devices and associated cerclage insertion instruments useful for repairing the skeletal system while overcoming the short comings identified in the surgical cable implant and instrument prior art. In accordance with one form of the article of invention, the clamping mechanism of the implant utilizes a multi-part (segmented) tapered collet that encircles the cable and is driven into a clamp body by a cannulated lock cap once a predetermined cable tension is established through the cable.

In some forms a multi-part collet is tapered on opposed ends of a collet to facilitate well distributed clamping pressure on a surgical cable through the entire length of a collet. Utilizing a cable fixation device with multi-part collet, a cable can be repeatedly locked and unlocked without damaging the cable or other portions of the cable fixation device.

In some forms, a system utilizes a clamp housing that fixes an enlarged head of a surgical cable within a head aperture located in the clamp housing.

In some forms, in an operative configuration the cable is looped around a bone segment using a surgical cable passer and reentered through a lock aperture in a clamp housing then through a collet and lock cap residing within the lock aperture. The cable cerclage loop and each of these aforementioned components share a collinear central axis situated within a single plane within a clamp housing therein preventing any torsion forces on the clamp body that may cause clamp housing to cant on a bone during tensioning and eliminating instrument handling difficulties and larger footprint associated with using a plurality of non-aligned instruments concurrently within a surgical corridor.

In some forms, sliding engagement is imparted between opposed faces on a lock cap and collets wherein advancing the lock cap does not impart rotation on the collet nor twist a surgical cable that could otherwise lead to cable failure.

In some forms a collet locking mechanism is non-abrasive and otherwise non-destructive to the cable providing the capability to repeatedly unlock and relock the cable without damage to the cable.

In some forms a cable fixation device is also configured for optional assembly during surgery in preferred embodiments. With this feature a cable may be passed in either direction through a cable passer.

In some forms a lock cap and housing of a cable fixation device comprise complementing frictional engagment features to prevent unintended back out and loosening of the locking cap. In preferred embodiments these complementing features are in the form of interfering features disposed on the lock cap and in some forms also on the housing of a fixation device.

Disclosed further are various embodiments of a cerclage insertion instrument.

In some forms, a cable fixation assembly may be loaded into or released from a clasp portion of a cerclage insertion instrument from a direction angled or preferably normal to the long axis of the instrument.

In some forms a clasp activator mechanism causes deflectable frame legs to deflect outward in a release configuration to provide for loading or release of a clamp housing in a clamp window.

In some forms a clasp activator mechanism causes deflectable frame legs to be locked to a predetermined clamp window width therein restraining a clamp housing between a pair of clamp arms.

In some forms restraint ribs (control arms) extending from opposing arm faces occupy control slots on a clamp housing.

In some forms restraint ribs are orientated perpendicular to a long axis of a frame body of a cerclage inserter instrument.

In some forms a clasp activator mechanism activates movement of a ram to cause deflection of frame legs.

In some forms a ram rides against a deflection cam to cause deflection of frame legs.

In some forms a ram comprises a pod channel for capture of a pod associated with frame legs to limit deflection thereof.

In some forms a ram is capable of linear axial movement when seated within an inserter frame of a cerclage inserter instrument.

In some forms a lock driver is disposed in a ram and the ram is disposed within an inserter frame wherein each component share a common elongate axis.

In some forms a ram component comprises a pivot bore at a proximal end for axial control of the ram.

In some forms a clasp activator mechanism comprises a lever mechanism articulating from a fixed pivot pin extending from an inserter frame.

In some forms a clasp activator comprises a lever mechanism articulating from a fixed pivot pin to drive a lever pin disposed in a ram.

In some forms a ram component comprises one or more ram horns extending from a distal end for control of a pair of deflectable frame legs.

In some forms, a ram component comprises a central aperture for occupation by a lock driver component.

In some forms, an inserter frame component comprises a near window for housing a provisional lock cap driver portion.

In some forms, an inserter frame component comprises a control mount on a proximal end for securing a control portion thereto.

In some forms a biased button or lever may be used to release the axial position of a lock driver.

In some forms a thumb wheel or cup may be used by a user to provide provisional locking of a lock cap in a cable fixation construct.

In some forms a control handle is releasably connected at a distal end of an inserter frame.

In some forms a control handle comprises a primary bevel gear and a complementing secondary bevel gear housed within.

In some forms said primary bevel gear is coupled to a lock driver.

In some forms said secondary bevel gear is coupled to a drive coupler.

In some forms said secondary bevel gear resides in a secondary bevel gear pocket of said control handle.

In some forms said primary bevel gear resides in a distal portion of a control pocket formed within said control handle.

In some forms a distal portion of said control pocket is threaded.

In some forms said control portion comprises a bearing and bearing race.

In some forms an outer radial wall of said bearing race is threaded.

In some forms threads on said bearing race complement said threads in distal portion of said control pocket for threaded engagment.

In some forms a torsion wrench engaged generally perpendicular to the long axis of a cerclage inserter instrument is used to impart torsional forces through a drive coupler, a bevel gear set, a lock driver, to a locking cap of a surgical cable fixation device.

BRIEF DESCRIPTION OF THE SEVERAL VIEWS OF THE DRAWINGS

These and other features and advantages of the present invention will become more readily appreciated when considered in connection with the following detailed description and appended drawings, wherein:

FIG. 10 is a top perspective view of a housing of the cable fixation device illustrated in FIG. 2;

FIG. 11 is a top view of a housing of a cable fixation device illustrated in FIG. 2;

FIG. 12 is front perspective view of a housing of the cable fixation device illustrated in FIG. 2;

FIG. 13 is top perspective view of a housing of the cable fixation device illustrated in FIG. 2;

DETAILED DESCRIPTION OF THE INVENTION

Figure 1:
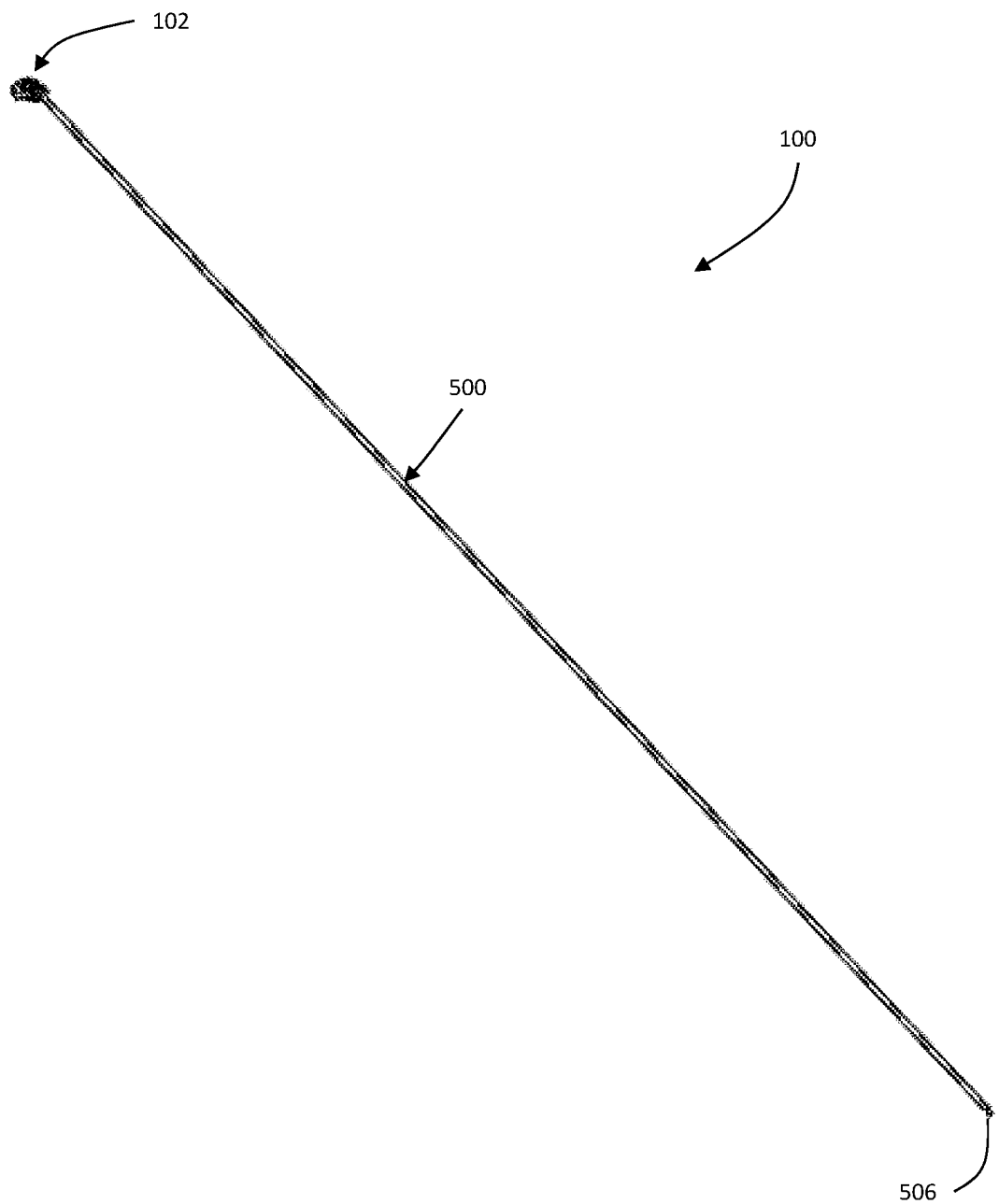
FIG. 1 is a perspective view of one form of a cable fixation device.
Figure 2:
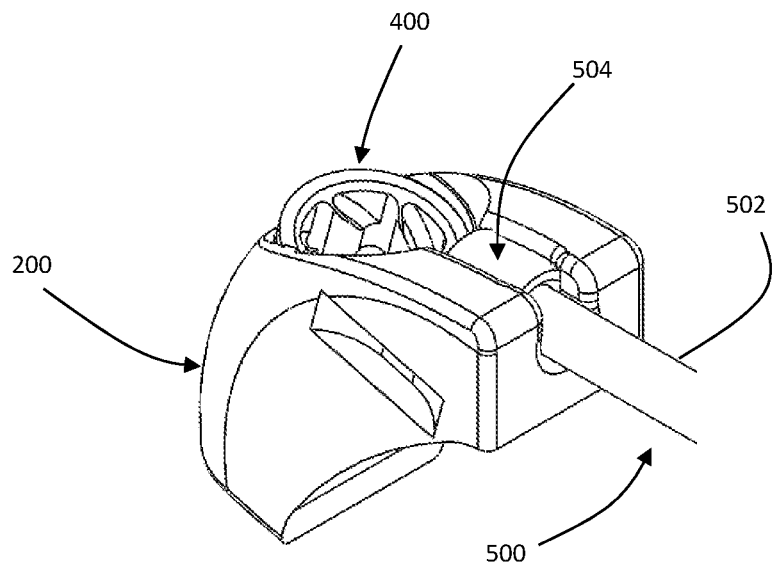
FIG. 2 is a close up perspective view of the locking portion of one form of a cable fixation device.

Referring to the Figures and written description, several exemplary embodiments of cable fixation devices, related instruments, and of methods of use thereof are disclosed herein.

In a preferred embodiment, one form of a cable fixation device 100 is illustrated in FIGS. 1-7. A cable fixation device 100 comprises a fixation assembly portion 102 and a cerclage cable 500 portion. A fixation assembly portion 102 comprises a clamp housing 200 portion, a cable collet 300 portion, and a lock cap 400 portion also referred to as a lock.

Figure 3:
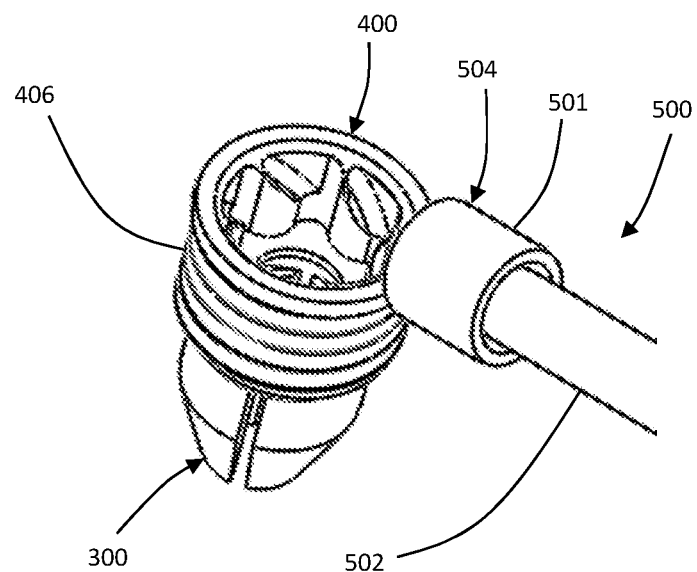
FIG. 3 is a perspective view of a cable fixation device illustrated in FIG. 2 with clamp housing removed.
Figure 4:
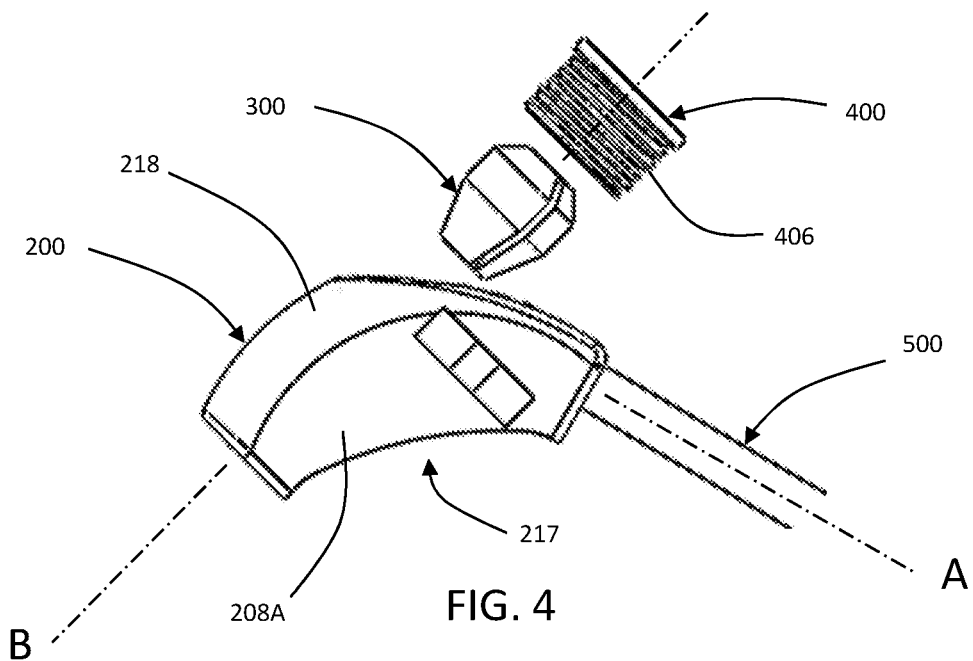
FIG. 4 is a side view of one form of a cable fixation device as illustrated in FIG. 2 with exploded locking cap and collet.

Each component of a cable fixation device 100 partially or fully resides within clamp housing 200. One end of cerclage cable 500 is enlarged as a cable head 504 and resides within clamp housing 200 in an operative configuration. In preferred embodiments, the cable head 504 is removable from clamp housing 200. In this embodiment (FIG. 3, shown without clamp housing), enlarged cable head 504 is in the form of a drum 501 fixed to the cable 502 end by friction, crimping, weld, or other methods.

As illustrated in FIGS. 4-13, clamp housing 200 comprises a block body 218 having a concave shaped 217 bottom surface 216 extending from a first side surface 208A to an opposed second side surface 208B. Concave shape 217 preferably has a concave radius slightly smaller than a bone surface it will be seated on. In alternative embodiments, concave shape 217 may be a generally flat surface extending between elevated opposing feet. Block body 218 comprises a front end surface 211 and a rear end surface 209. Protruding adjacent the junction of front end surface 211 and bottom surface 216 is one or more first feet 215A. Protruding adjacent the junction of the rear end surface 209 and bottom surface 216 is one or more second feet 215B. In some embodiments, first and second feet may be sharpened or extended into the form of teeth and serve to prevent slippage across the surface of a bone once implanted on bone and cable tensioned.

Extending towards front surface 211 of body 218 along axis 'A' (FIG. 9, 11) is head aperture 212 defining head walls 205 sized to house cable head 504 which here is in the form of a cable drum 501 of cable 500. Cable shelf 219 with head stop surface 220 contain drum 501 in head aperture 212 and prevent it from being pulled out of the housing when the cable 502 is tensioned. Cable slot 213 is sufficiently wide for the loading of cable 502 into head aperture 212 wherein the cable drum 501 is then seated in head aperture 212 upon pulling of the free end of cable 500.

Figure 5:
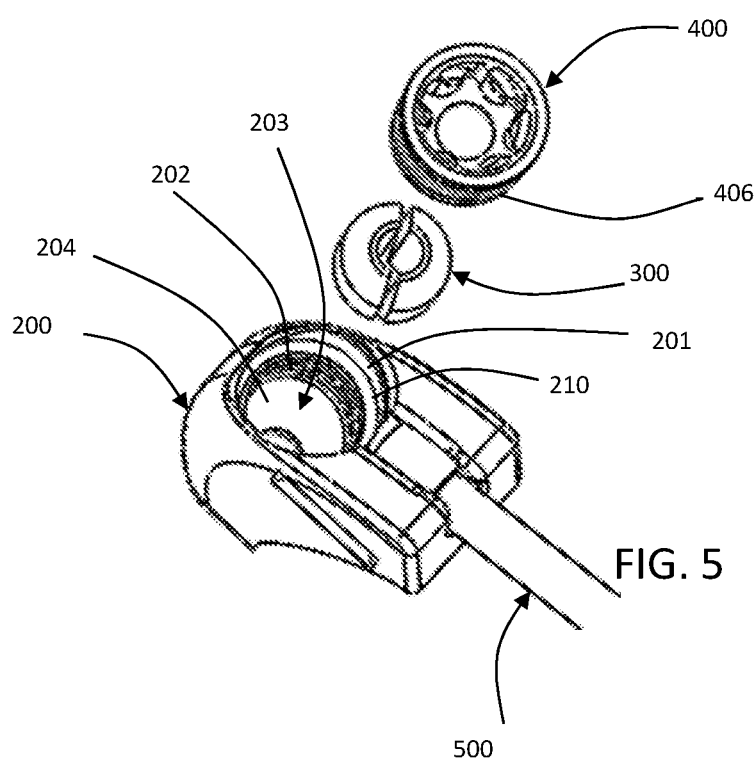
FIG. 5 is a top perspective view of a cable fixation device illustrated in FIG. 2 with exploded locking cap and collet.
Figure 6:
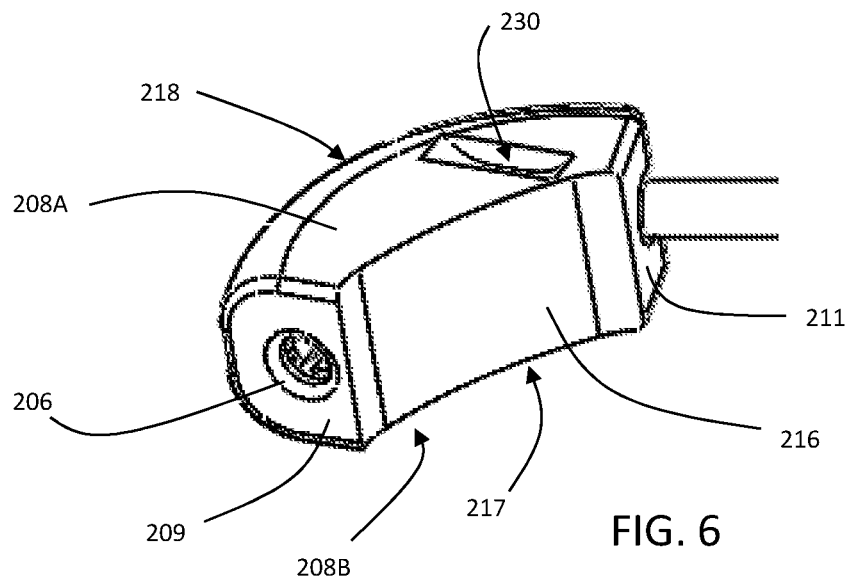
FIG. 6 is a bottom perspective view of a cable fixation device illustrated in FIG. 2.
Figure 7:
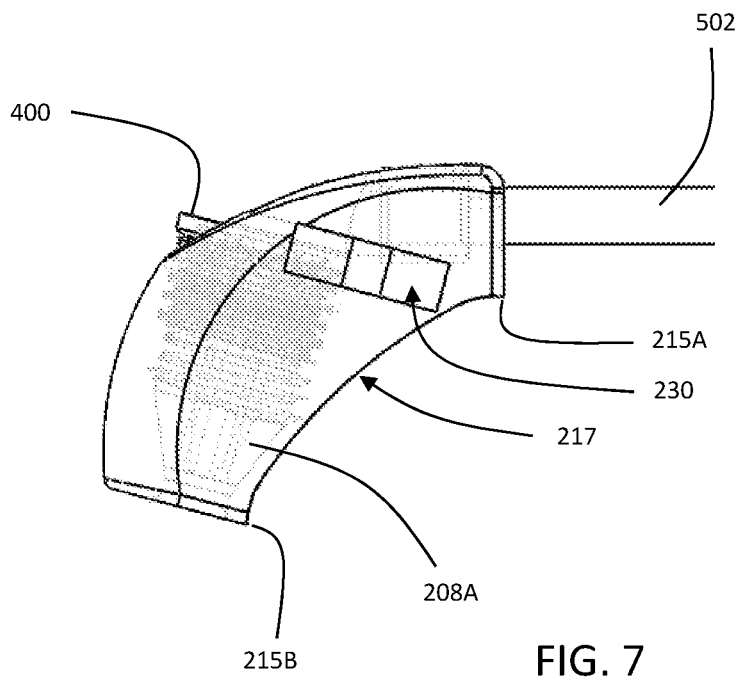
FIG. 7 is a side semitransparent view of a cable fixation device illustrated in 2.
Figure 8:
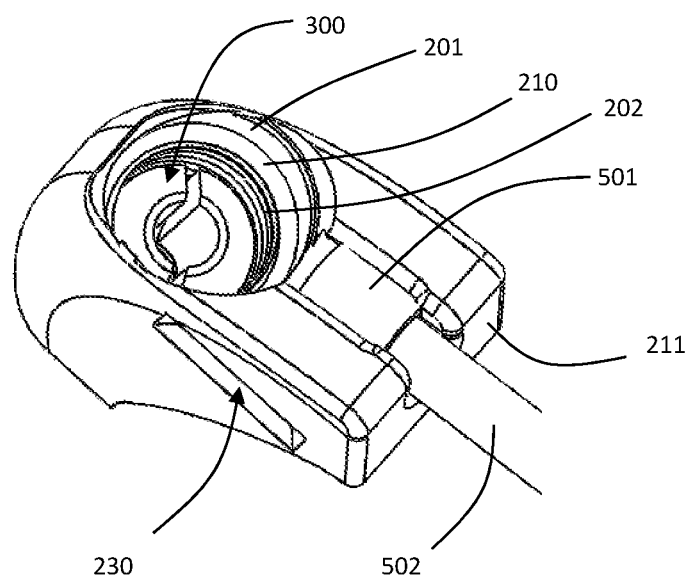
FIG. 8 is a top perspective view of a cable fixation device illustrated in FIG. 2 with locking cap removed.
Figure 9:
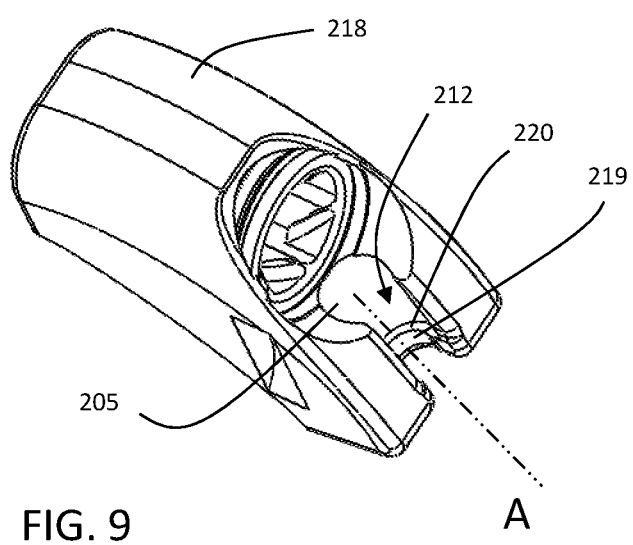
FIG. 9 is a front perspective view of a cable fixation device illustrated in FIG. 2 with cable removed.
Figure 14:
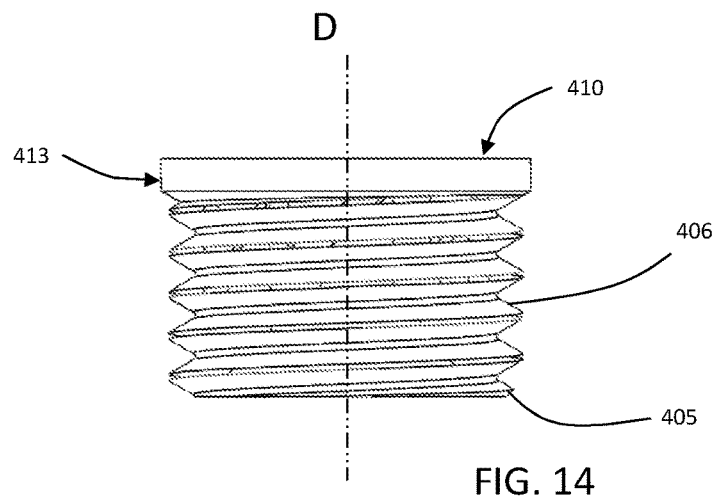
FIG. 14 is a side view of one form of a locking cap to illustrate threads.

Lock aperture 203 defines a series of walls with surfaces having various diameters as illustrated in FIGS. 5 and 10. Passage wall 201 is sized of sufficient diameter to freely pass cable 502, cable collet 300, and lock cap 400. A step 210 draws in to fixation wall 202. Fixation wall 202 comprises features to fix lock cap 400 in place and in this embodiment is in the form of threads for engagement with threads on opposed cap fixation wall 406 of lock cap 400. Compression wall 204 is tapered or may be stepped and complements second lock wall 305B (FIG. 18) of collet 300 wherein when lock cap 400 is threadably advanced, lock wall 305B is driven along axis C therein causing each component of collet 300 to move towards each other to clamp against and fix cable 502 in place within clamp housing 200. Formed within block body 218 is inlet wall 206. It is sized sufficiently large to freely pass cable 502 while small enough to prevent passage of collet 300. The portion of inlet wall 206 adjacent rear end surface 209 may be tapered as illustrated in the embodiment of FIG. 12 to assist loading of cable 502 therethrough.

In body 218 of housing 200 is one or more control features for use by an instrument for control of body 218 during implantation. In this embodiment (FIG. 6-7) a control feature is in the form of control slots 230 inscribed in opposing first and second side surfaces 208A and 208B. Portions of an instrument occupy these slots during insertion of the implant. In alternative embodiments, control slots 230 may be open at one end. The slot may be internally rounded to ease insertion and release of the instrument. In preferred forms the elongate side of the slot is perpendicular to the locking cap drive axis (Axis B) for improved functionality in minimally invasive procedures. In this manner, loading and unloading of housing 200 in and out of an insertion instrument is performed generally perpendicular to the surgical axis thereby providing the surgeon capability to advance or retract the insertion instrument and implant along the surgical axis with little fear of an implant unintentionally releasing from an instrument.

In this embodiment, a preferred axis of implant insertion is generally coincident to axis B. In preferred forms, an insertion instrument used to insert a fixation assembly portion 102 will also have an elongate axis generally parallel if not coincident with Axis B. This arrangement between instrument and implant minimizes the necessary diametrical profile of the implant and instrument during insertion and consequently minimizes the diameter of incision required resulting in reduced surgical tissue damage. Despite these advantages, in other forms the elongate side of the slot may be positioned parallel or at a different predetermined angle to the locking cap drive axis. In other forms, a control feature may take the form of a boss or ridge.

Figure 18:
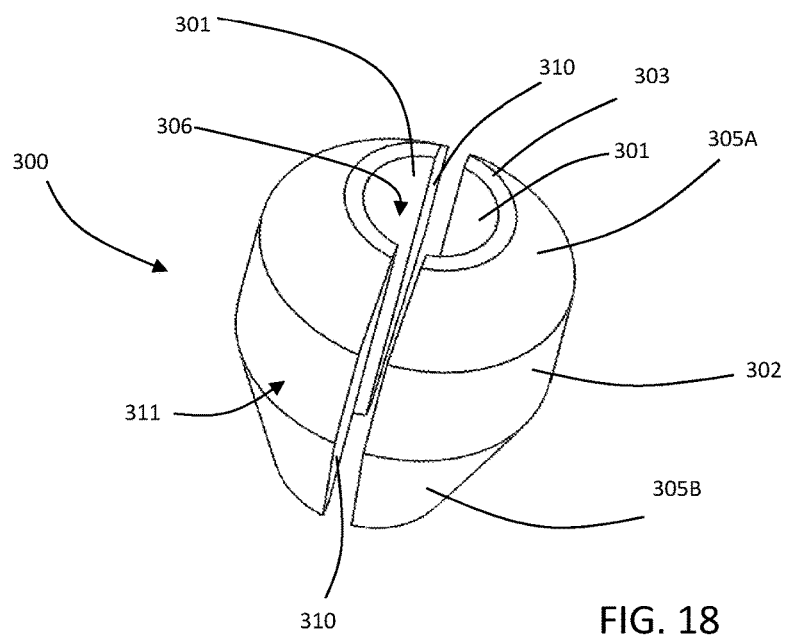
FIG. 18 is a perspective view of one form of a multipart collet.
Figure 19:
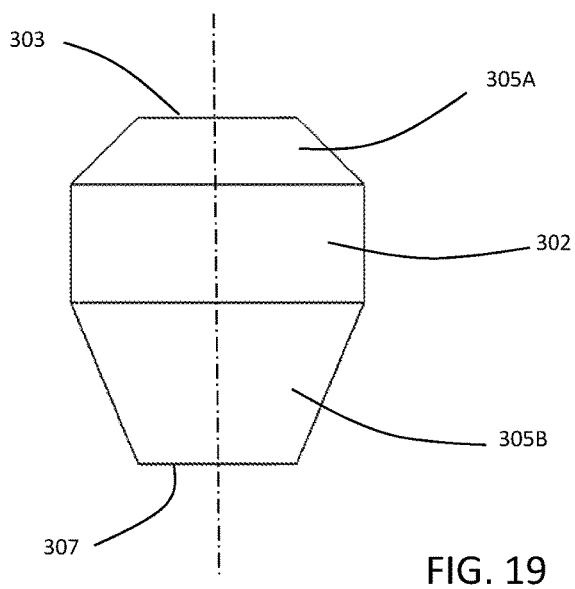
FIG. 19 is a side view of one form of a multipart collet.
Figure 19A:
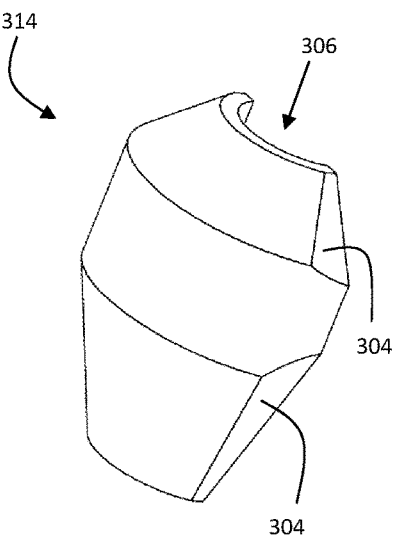
FIG. 19A is a top perspective view of one form of one section of a multipart collet.

Cable collet 300 is illustrated in FIGS. 18-19. The collet 300 in this embodiment comprises two or more collet sections 314 as illustrated in FIG. 19A. Each collet section 314 is preferably a duplicate of each other and when assembled substantially from a 360 degree cable collet 300. Each collet section 314 comprises a curved body 311 with central aperture 306 extending therethrough along axis 'C' defining cable surface 301. When cable collet 300 is in an uncompressed configuration (unlocked) central aperture 306 is sufficient in diameter to pass cable 502. In a compressed configuration (locked) central aperture 306 is reduced wherein cable lock surface 301 binds against cable 502 preventing the cerclage loop from loosening. The body 311 comprises a bottom face 307, a top face 303, a first lock wall 305A, a second lock wall 305B, and a head face 302. The body 311 may comprise other tapered surfaces such as assembly taper 304 used to prevent binding by the collet on other structures during assembly or when transitioning between compressed and uncompressed configurations. Each collet section 314 comprises one or more gap walls 310. Gap walls of opposing collet sections are spaced by a gap that reduces in width as the collet is compressed about the cable 502 during locking.

Figure 15:
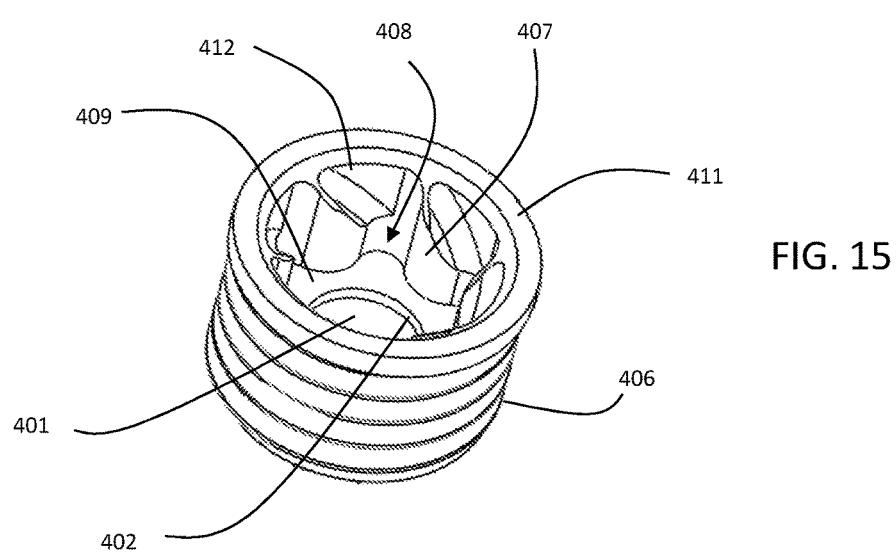
FIG. 15 is a top perspective view of a locking cap illustrated in FIG. 9.
Figure 15A:
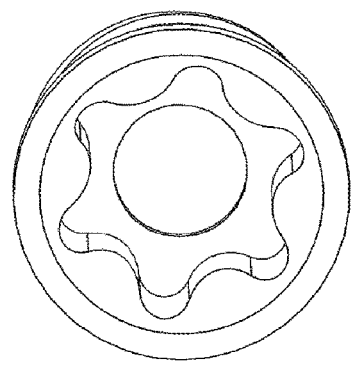
FIG. 15A is a top perspective view of an alternative form of a locking cap.
Figure 16:
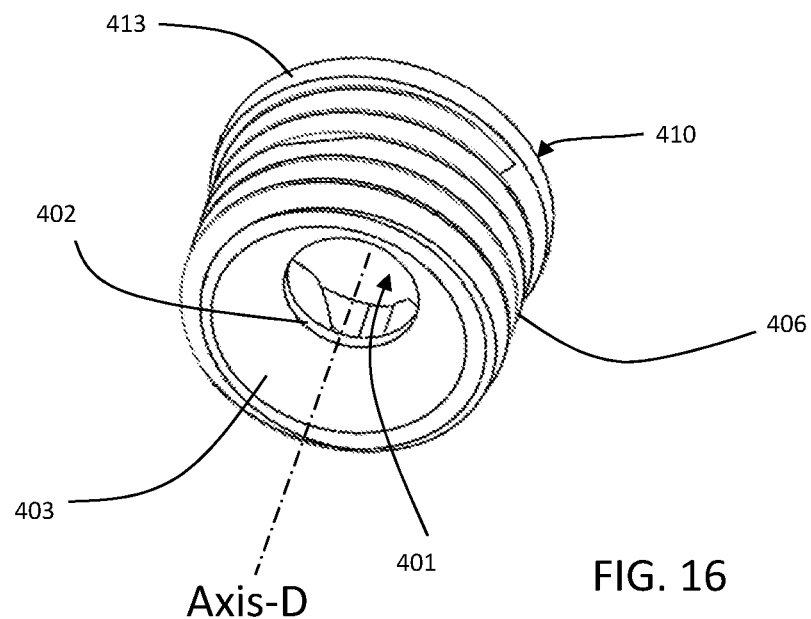
FIG. 16 is a bottom perspective view of a locking cap illustrated in FIG. 9.
Figure 17:
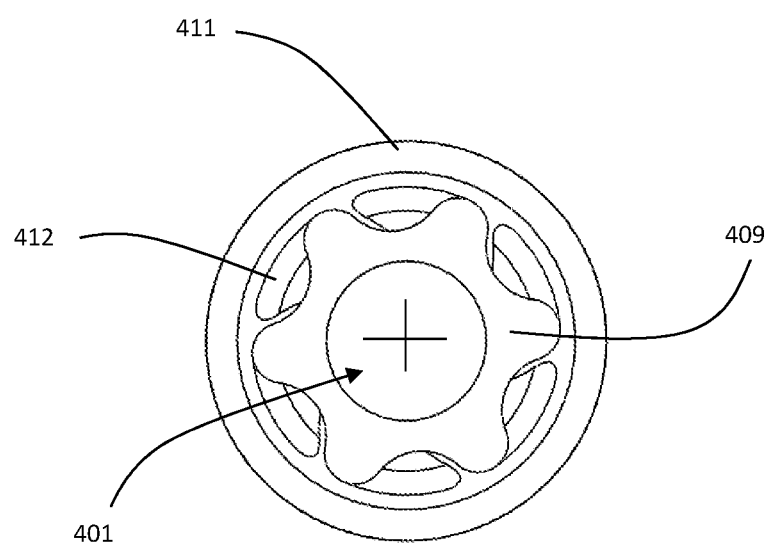
FIG. 17 is a top view of a locking cap illustrated in FIG. 9.

Lock cap 400 (FIG. 14-17) comprises a cylindrical body 410 with axis aperture 401 extending along axis D. Extending from top surface 411 is drive pocket 408 configured to receive a driver tip from an instrument. Drive pocket 408 defines drive surfaces 407. At the bottom of drive pocket 408 is pocket base 409. Axis aperture 401 is sufficient in diameter to pass cable 502 through compression wall 403 and defines cable wall 402. Compression wall 403 is configured to complement first lock wall 305A of collet 300 to cause each collet section to move toward central axis C as lock cap 400 is advanced. For example compression wall 403 may be stepped or sloped as illustrated in FIG. 16. Cap fix wall 406 of lock cap 400 engages fixation wall 202 of clamp housing 200 for locking. In this embodiment, fix wall 406 and fixation wall 202 have complementing threads. Threads on fix wall 406 may include a lead-in taper 405 to ease starting of threads. Drive lead 412 comprises a plurality of sloped surfaces drafted downward from top surface 411 to a predetermined depth within drive pocket 408. The drive lead 412 eases alignment and insertion between the head of a driver instrument as the user attempts to insert it into drive pocket 408. Drive lead 412 is absent in alternative embodiments such as illustrated in FIG. 15A.

Cerclage cable 500 comprises a cable 502, a cable drum 501 at cable head 504, and a cable lead (FIG. 1). The cable lead is the free end of the cable and comprises a swaged rounded tip to keep all cable strands tightly wound for eased entry into cable apertures.

Figure 20:
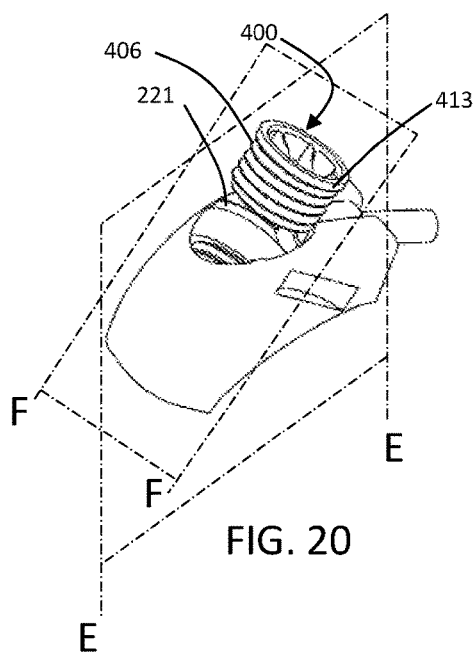
FIG. 20 is a top perspective view of one form of a locking cap pre-assembled with a housing of a cable fixation device.
Figure 21:
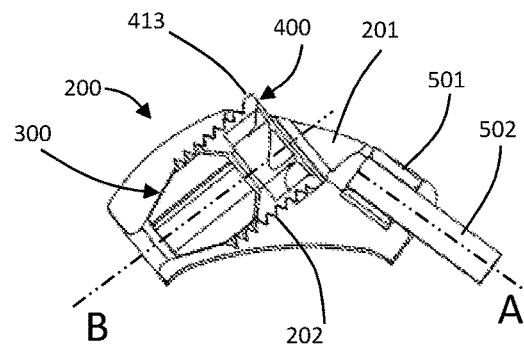
FIG. 21 is a cross-sectional view across plane E-E of one form of cable fixation device in an operative configuration.
Figure 22:
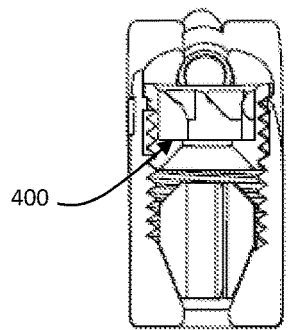
FIG. 22 is a cross-sectional view across plane F-F of one form of a cable fixation device as a locking cap is partially advanced into a housing.
Figure 23:
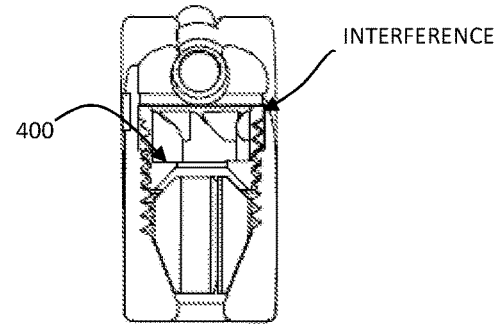
FIG. 23 is a cross-sectional view across plane F-F of one form of a cable fixation device as a locking cap is nearly fully advanced into a housing and illustrating an interference fit between to lock cap and housing to prevent lock cap backout.

FIGS. 21-23 illustrate various cross-sectional views of one form of a cable fixation device illustrated in FIG. 20. In addition, these views illustrate preferred forms of a cable fixation device having a locking cap anti-back out feature. Surfaces formed on a friction wall 221 (previously passage wall 201) of housing 200 and on interference boss 413 of lock cap 400 are configured for frictional interfere with each other as lock cap 400 approaches full advancement to a locked configuration. Frictional forces created between the interference boss 413 and frictional wall 221 are sufficient to prevent unintended back out of lock cap 400 yet requires minimal additional advancement force to overcome the friction during locking and unlocking. As illustrated in the embodiment of FIG. 20, interference boss 413 is in the form of a protruded ring shaped ridge having a diameter slightly larger than the major diameter of fix wall 406 on locking cap 400. Also in FIG. 20 is friction wall 221 illustrated in the form of a flat annular surface having a diameter slightly smaller than the surface of interference boss 413.

FIG. 21 is a cross-sectional view through plane E-E illustrating a locking cap 400 as it is advanced down fixation wall 202. FIG. 22 is a cross-section view through plane F-F along axis B illustrating advancement of lock cap 400 prior to interference occurring between friction wall 221 and interference boss 413. FIG. 23 illustrates further advancement of the lock cap 400 just as interference begins to occur between interference boss 413 and friction wall 221. Advancement of lock cap 400 will continue until fully compressed against collet 300 to fix position of cable 502 and thus preventing release of cable tension.

The cable fixation device 100 is preferably pre-assembled for surgery with collet 300 loosely seated within compression walls 204 and lock cap 400 partially threaded within fixation wall 202. The cable drum 501 is pre-seated within drum walls 205. A cable fixation device 100 is utilized by wrapping a free end of a cable around the bone or bone segments to be stabilized. A cable passer may be utilized for this purpose. Free cable lead 506 end of cable 502 is fed through inlet wall 206 of clamp housing 200, through the central aperture 306 of the collet, through an axis aperture 401 of cable wall 402 of lock cap 400, through a central cable aperture of a driver tip, and finally into adjacent cable tensioner tool (not shown) abutting tensioner face of a cannulated driver.

Slack in cable 502 is removed and the tensioner is clamped on the cable. The cable is tightened to a predetermined amount therein causing the cerclage loop around the bone to tighten and feet 215 to engage the bone surface. At this point the surgeon rotates handle to drive lock cap 400 into threaded housing therein compressing collet 300 against cable 502 and locking construct at specified tension. If the surgeon chooses, driver handle may be derotated to loosen and remove the cable fixation device 100 or to retension to an alternative tension level before relocking.

Figure 24:
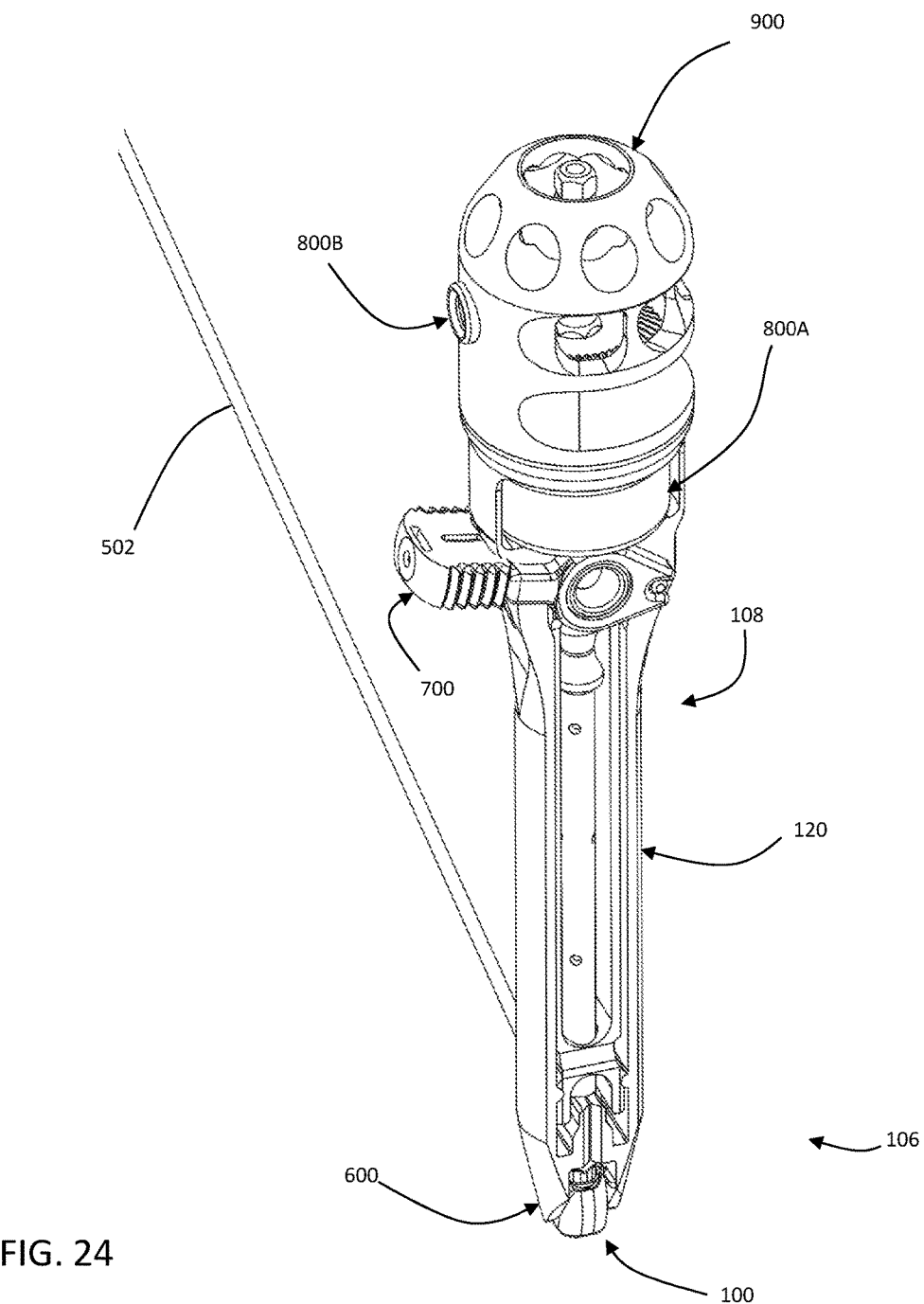
FIG. 24 is a top perspective view of a cerclage insertion device clasping a cable lock and a portion of a cable implant.

One embodiment of a cable implant inserter construct 106 is illustrated in FIG. 24. The construct 106 is illustrated comprising a cerclage inserter 108 instrument portion engaged with a cable fixation device 100 implant. In this embodiment cerclage inserter 108 comprises an implant clasp portion 600, an engagement activator 700 portion, a provisional 800A and final 800B locking cap driver portion, and a control portion 900. Cerclage inserter frame 120 houses many of the inserter 108 components.

Clasp portion 600 in this embodiment is in the form of a deflectable clamp operable to secure or release a clamp housing 200 therein. Clasp portion 600 is driven by a clasp activator 700 illustrated here in the form a lever 770 (FIG. 27) extending from a side of inserter instrument 108. Proximal directed forces by a user on lever 770 causes inserter 108 to operate in a release configuration whereby fixation assembly portion 102 is free to release from inserter instrument 108. Distally directed forces by a user on lever 770 causes inserter 108 to operate in a hold configuration whereby clasp portion 600 restrains fixation assembly 102 to inserter instrument 108.

Figure 31:
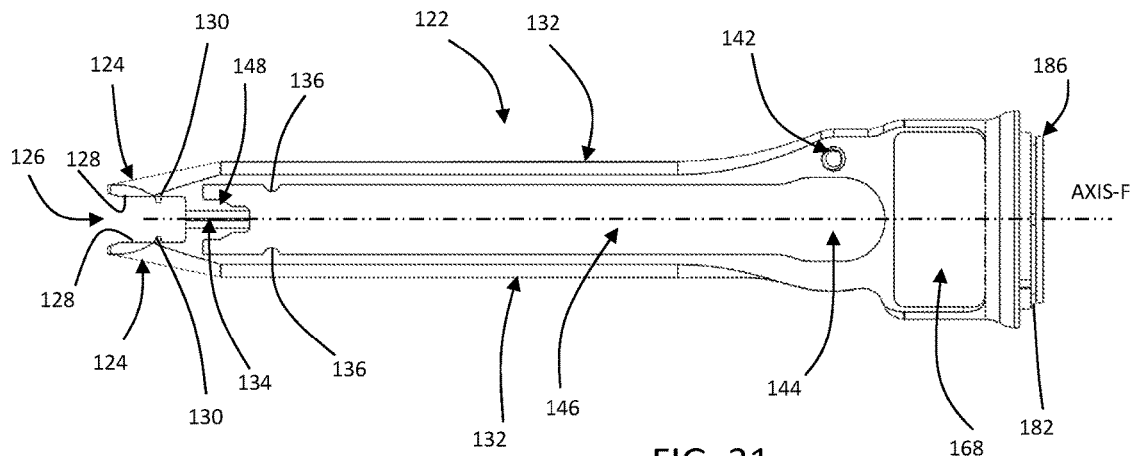
FIG. 31 is a side view of a preferred embodiment of a inserter frame.
Figure 32:
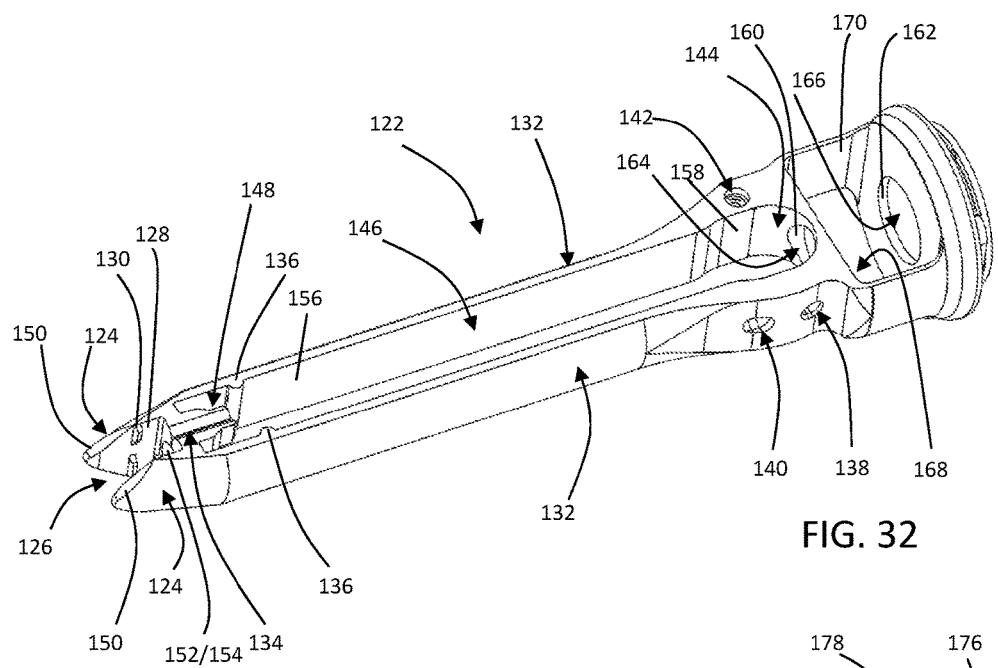
FIG. 32 is a perspective view of an inserter frame illustrated in FIG. 31.

Cerclage inserter frame 120 is illustrated in FIGS. 31 and 32. Frame 120 comprises a frame body 122. Extending from a distal end of body 122 are a pair of opposed elongate clasp arms 124 (also referred to as a clamp base) defining a pair of opposed arm faces 128 which in turn define a clamp window 126. Clasp window 126 has size and profile to fit clamp housing 200 therein. Extending from arm faces 128 are one or more opposed restraint ribs 130 (also known as control arms) also with size and profile for fit within control slot 230. In this embodiment, arm faces 128 comprise a plurality of restraint ribs 130 that are generally rectangular in shape and orientated perpendicular to elongate axis-F that extends through inserter frame 120. Restraint ribs 130 may comprise a lead-in taper at one or more ends of the rib 130 to ease loading or removing a fixation assembly portion 102 from clamp window. In some embodiments, two or more restraint ribs 130 are aligned and extend from an arm face 128. Clasp arm 124 may also be distally tapered, rounded, or both to ease movement of inserter instrument 108 through soft tissue during surgery.

Extending from opposed frame legs 132 is pod 148 just proximal clamp window 126. Relief channel 134 divides pod 148 serving to facilitate opposed frame legs 132 to deflect inward or away from Axis-F. Extending through pod 148 along Axis-F is pod passage face 152 which defines a pod aperture 154 therein.

Proximal to pod 148 are opposed long faces 156 defining long aperture 146. Long face 156 continues proximal and merges with slide face 158 to define slide aperture 144. Adjacent slide aperture 144 within one of frame legs 132 is pivot recess 142 configured for receiving a threaded or pressed pin. Disposed on a lateral surface of an opposed frame leg 132 is a distal lever notch 140 and spaced proximal a proximal lever notch 138. Intermediate face 160 defines intermediate aperture 164 and proximal face 162 defines proximal aperture 166. Extending through frame body 122 between intermediate face 160 and proximal face 162 is provisional face 170 defining provisional aperture 172.

Figure 32A:
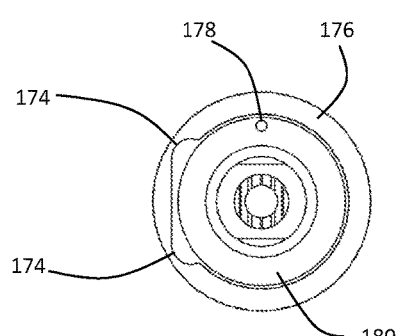
FIG. 32A is a proximal end view of an inserter frame illustrated in FIG. 31.
Figure 33:
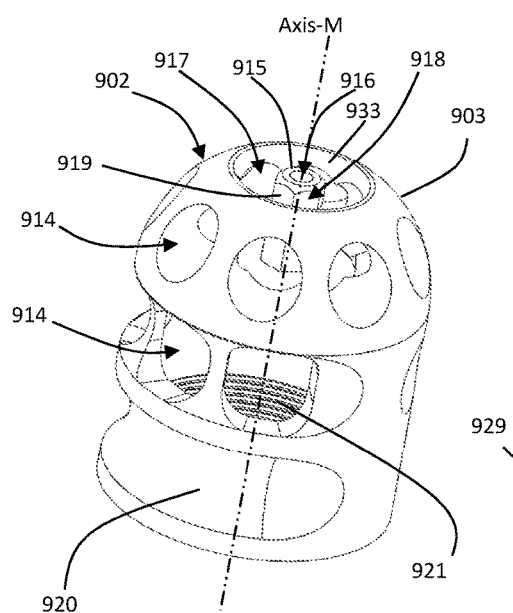
FIG. 33 is a proximal perspective view of a preferred embodiment of a control handle which houses internally several components of a control portion.
Figure 34:
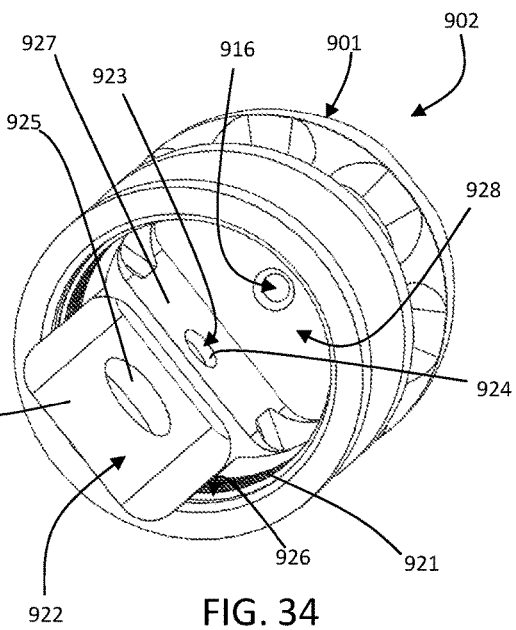
FIG. 34 is a distal perspective view of a control handle illustrated in FIG. 33.
Figure 35:
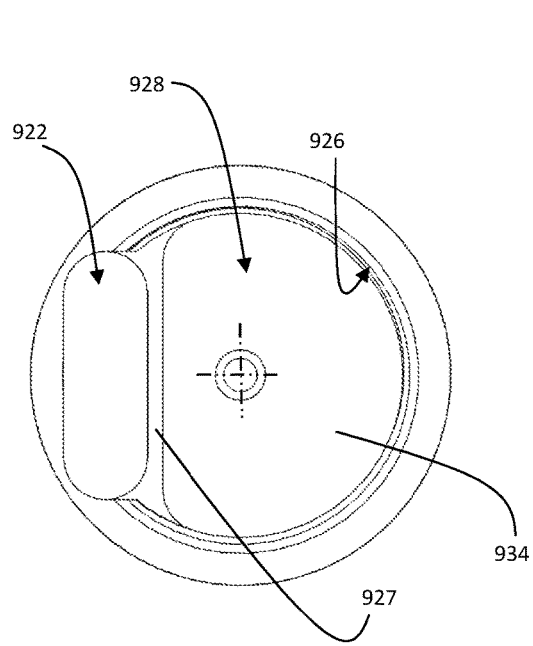
FIG. 35 is a distal view of a control handle illustrated in FIG. 33.
Figure 36:
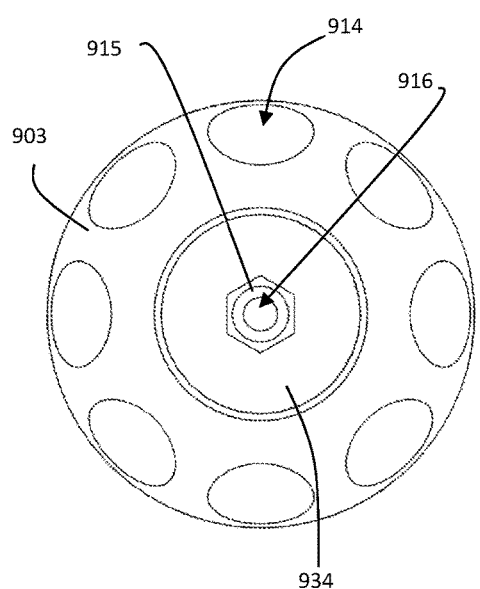
FIG. 36 is a proximal view of a control handle illustrated in FIG. 33.

Disposed on the proximal end of frame body 122 are features to secure and orientate a control portion 900 to frame body 122. Control positioner 174 is raised into control 900 and orientates the rotational and center position of control portion 900 along Axis F. Control face 176 abuts control portion 900. Pin pocket 178 houses a race pin 911 extending proximally for alignment of a control race 908. Bearing face 180 situated normal to Axis F provides a flat surface for rolling of bearings. FIG. 32A also illustrates a variety of apertures as defined earlier extending along Axis-F through frame body 122.

Figure 28:
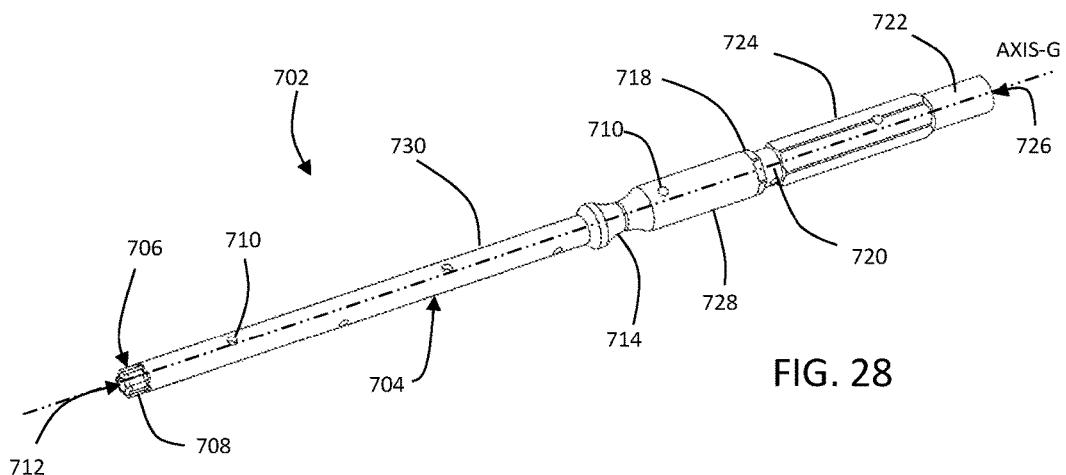
FIG. 28 is a perspective view of a preferred embodiment of a lock driver.

A clasp activator 700 of cerclage inserter 108 comprises a series of components that work together to engage and disengage a lock driver 702 with a lock or locking cap of a cable fixation device 100. One embodiment of a lock driver 702 is illustrated in FIG. 28. Driver 702 comprises a cannulated rod 704 with central axis-G and with a driver head 706 at a distal end. Driver head 706 comprises drive faces 708 configured to engage complementing drive surfaces 407 in drive pocket 408 of lock cap 400. In a preferred embodiment, drive faces 708 form a multi-lobe profile. Cannulated rod 704 is perforated along its length with cleaning apertures 710 extending from an outer surface to an inner cannula 712 which extends end to end. A finger wheel 714 portion is provided for a user to adjust the axial position or radially adjust driver 702 to ease insertion into a lock cap. First crank faces 724 are configured for sliding engagement with a bevel gear that is part of a final locking cap driver portion 800B. In this embodiment, first crank faces 724 are in the form of a hex profile as are second crank faces 718 which are spaced distally from first crank faces 724 by mid groove 720. First crank faces 724 and second crank faces 718 are aligned. Proximal to first crank faces 724 is proximal axial surface 722. Mid axial surface 728 is positioned between finger wheel 714 and second crank faces 718. Butt face 726 resides on the proximal end of driver 702.

Figure 29:
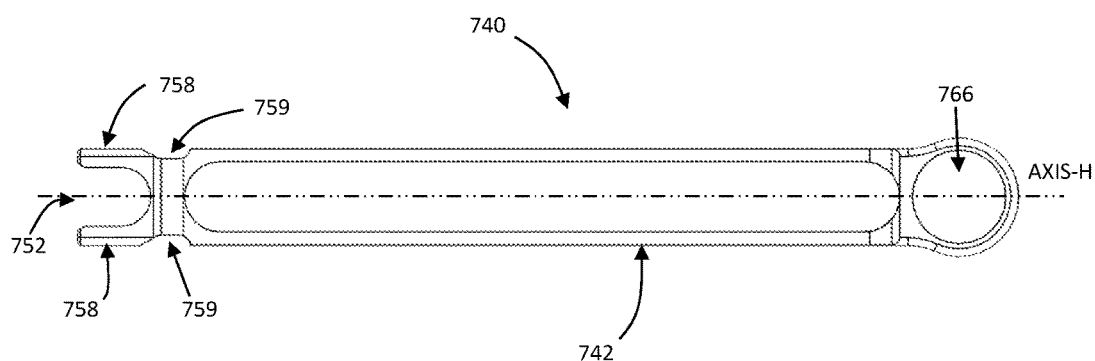
FIG. 29 is a side view of a preferred embodiment of a ram.
Figure 30:
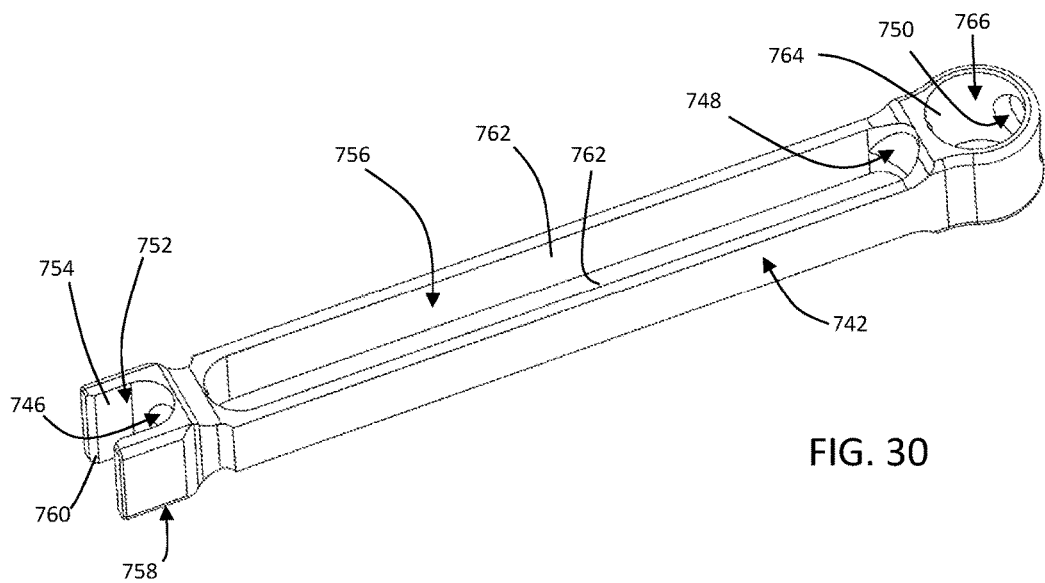
FIG. 30 is a perspective view of ram illustrated in FIG. 29.

A ram 740 is housed within a long aperture 146 and slide aperture 144 of frame body 122. One embodiment of a ram 740 is illustrated in FIG. 29-30. Ram 740 comprises a ram body 742. A bore 744 of various diameters extends down the length of ram 740 along axis-H forming a first aperture 746 at a distal end, a second aperture 748 offset from a proximal end, and a third aperture 750 at a proximal end. Pod channel 752 extends into a distal end of ram body 742 and is defined by opposing channel faces 754. Pod channel 752 is sized and shaped for fit over pod 148 of inserter frame 120 in a hold configuration therein causing channel faces 754 to bind against opposing outer sides of pod 148 thereby limiting outward deflection of frame legs 132 such that clamp housing 200 may be held firmly within clamp window 126. Entry taper 760 is used along with tapers on pod 148 to ease movement of ram 740 as it is forced distally against pod 148.

First aperture 746 is sufficient in diameter to slidingly house main rod 730 portion of cannulated rod 704. Second aperture 748 and third aperture 750 are sufficient in diameter to slidingly house mid axial surface portion 728. A view aperture 756 extends through ram body 742 and is defined by opposing view faces 762. Pivot face 764 defines pivot bore 766 which extends through ram body 742 at a proximal end.

Figure 27D:
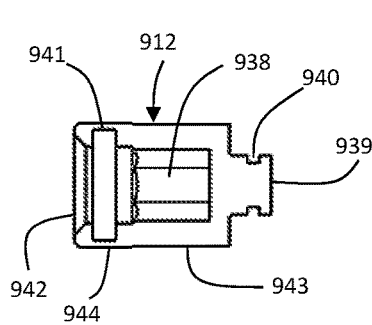
FIG. 27D is a cross sectional view through a mid-plane of a drive coupler.
Figure 27A:
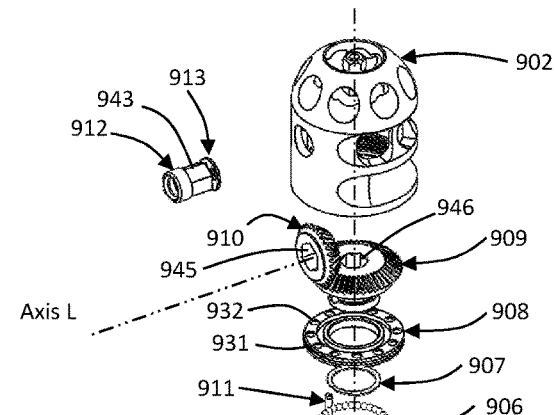
FIG. 27A is a top perspective view of a preferred embodiment of a clasp activator.
Figure 27A:
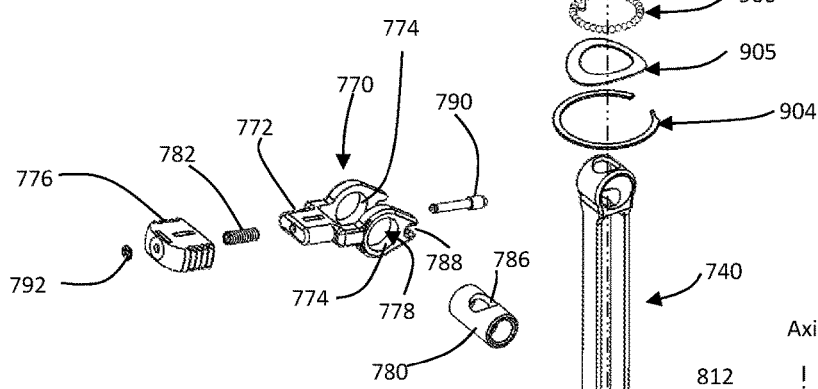
Figure 27A:
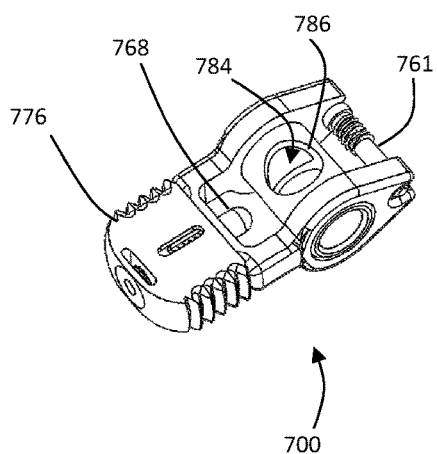
Figure 27:
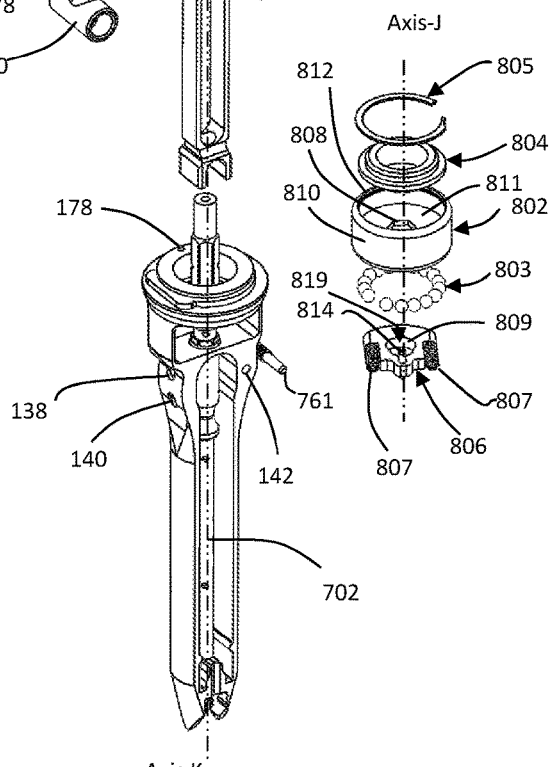
FIG. 27 is an exploded view of a preferred embodiment of a cerclage inserter instrument.
Figure 27C:
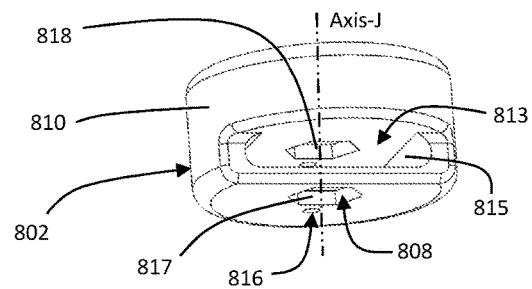
FIG. 27C is a perspective view of a preferred embodiment of a thumb cup.

A clasp activator 700 of cerclage inserter 108 comprises a series of members cooperating to control ram 740 causing clasp 600 to transition between hold and release configurations. Clasp activator 700 comprises in one embodiment a lever 770 extending from a cerclage inserter 108. In preferred forms the lever is saddle shaped as illustrated in FIGS. 27 and 27A. Lever 770 comprises a lever handle 772 portion extending from a pair of opposed pivot rings 774. Lever handle 772 may be covered by lever cap 776. Each pivot ring 774 comprises a pivot bore 778 of a diameter sufficient to house lever pin 780. Extending generally perpendicular through lever pin 780 is drive bore 784 defined by drive bore walls 786 having diameter sufficient to pass mid axial surface 728 of lock driver 702. Lever spring 782 cooperates with spring pin 790 and spring clip 792 to form a functional spring pin. Spring pin head 794 engages proximal and distal lever notch 138 and 140 to releasably hold in one position or other notch therebetween to activate a release or hold configuration. Fixed pivot channel 788 extends across both pivot rings 774 and is sized to pivot about fixed pivot pin 761 extending from pivot recess 142 in frame body 122.

Figure 25A:
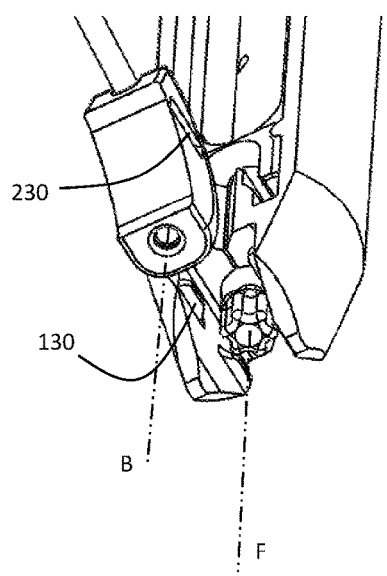
FIG. 25A is a close up perspective view of a cable fixation device preparing to be clasped by a cerclage insertion device.
Figure 25:
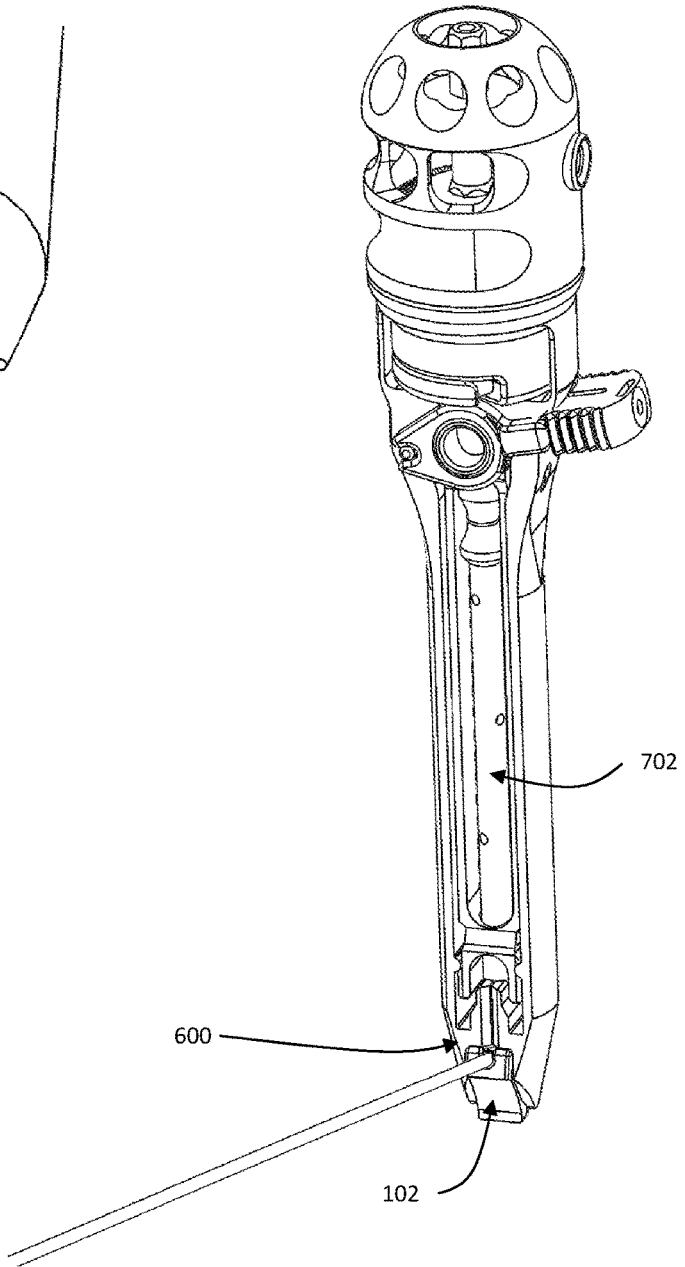
FIG. 25 is side perspective view of a cerclage insertion device clasping a cable lock and a portion of a cable implant.
Figure 26A:
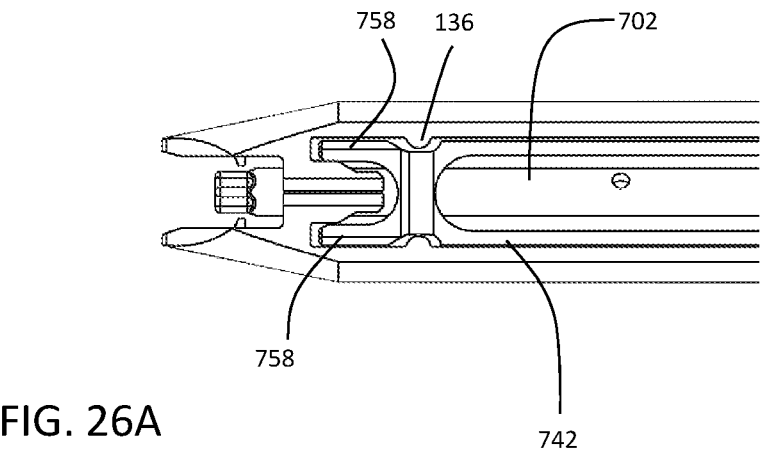
FIG. 26A is a side view of a distal end portion of a cerclage inserter instrument illustrating the interaction between a ram and inserter frame portion.
Figure 26:
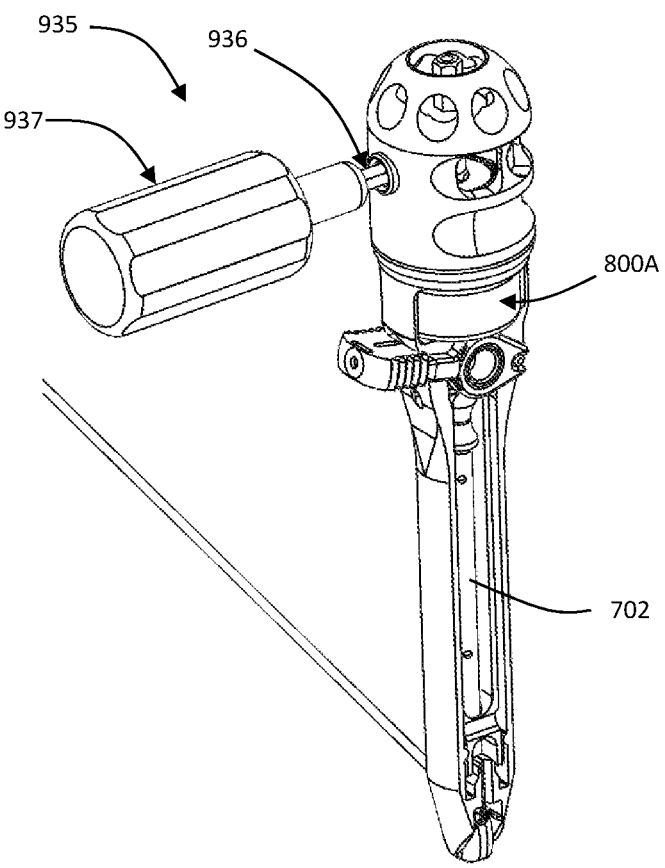
FIG. 26 is a top perspective view of one embodiment of a cable implant inserter construct illustrating a torsion wrench engaged for advancing lock driver 702.

FIG. 26A illustrates the distal end of cerclage inserter 108 when in a hold configuration. Ram horns 758 enclose pod 148 therein preventing separation of frame legs 132 and consequently firmly holding clamp housing 200 (not shown) within clamp window 126. Deflection cams 136 are resting within the respective cam pockets 759. Activation of lever handle 772 to release configuration will cause ram 740 to move proximally and away from pod 148. Deflection cams 136 are forced out of cam pockets 759 causing a consequent outward deflection of frame legs 132 therein widening clamp window 126 for removal of cable fixation device 100. In this release configuration, clamp housing 200 and remaining members of cable fixation device 100 may also be loaded into clamp window 126 (FIG. 25A) by aligning restraint ribs 130 with control slots 230 and moving housing 200 to a position of alignment between axis-F and axis-B as illustrated in FIG. 25. Housing 200 is then firmly held in this position by activation of lever 770 to a hold configuration.

Figure 38:
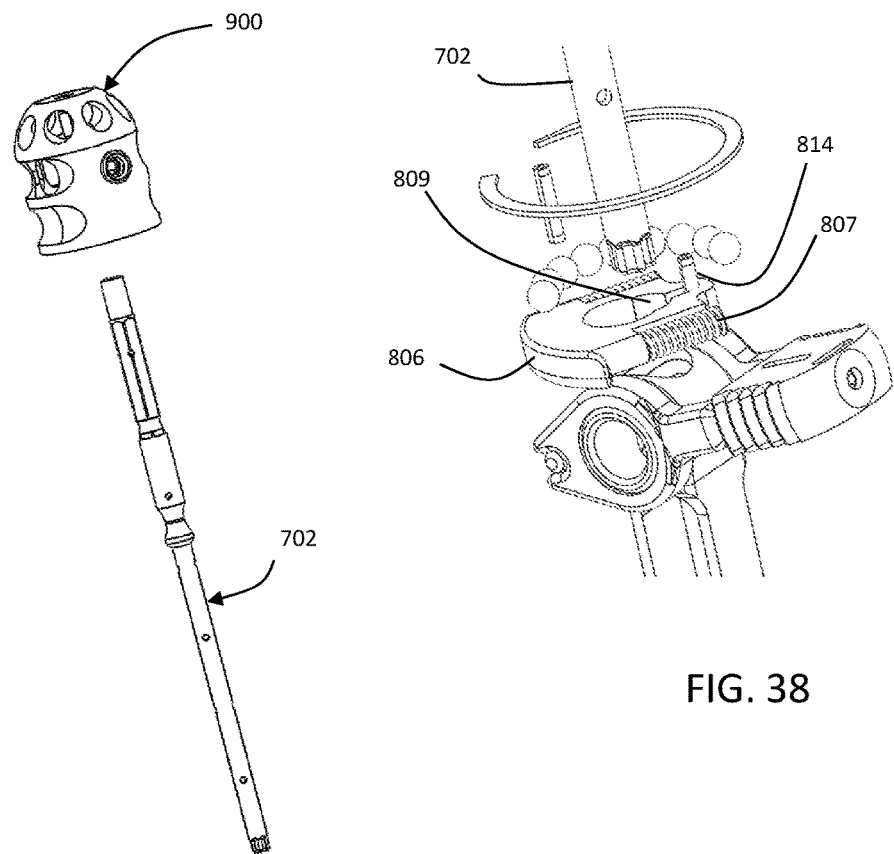
FIG. 38 is a perspective view of a portion of an instrument disassembly button with parts removed

A provisional locking cap driver portion 800A may be utilized to provide provisional locking of a lock cap 400. One embodiment of this assembly is illustrated in FIGS. 26, 27, 27B, and 27C. Provisional lock driver portion 800A comprises a thumb cup 802 having an engagement bore 808 extending through the middle of cup 802 along a central axis-J with distal engagement face 817 configured to engage second crank face 718 and proximal crank face 818 configured to engage first crank face 724 on lock driver 702. Disassembly button 806 and springs 807 reside in button receiver 813. Restraint pin 814 disposed in restraint pin aperture 816 holds button 806 within button receiver 813. Springs 807 bias button 806 away from receiver wall 815 which defines the three enclosed radial sides of button receiver 813. As a consequence, button wall 809 is forced against mid groove 720 of lock driver 702 keeping driver head 706 of lock driver 702 extended in drive pocket 408 of lock cap 400. FIG. 38 illustrates button 806 operation with benefit of several components removed.

When assembled and in an operational mode, imparting a rotary force by the user on thumb face 810 will result consequential rotation of lock driver 702 and advancement of lock cap 400. Distal bearing 803 is sandwiched between inner floor 811 of thumb cup 802 and distal bearing race 804. Thumb restraint 805 snapped into cup rim 812 holds this assembly together. (Distal bearing 803 is erroneously shown below thumb cup instead of inside adjacent inner floor—see FIG. 27B).

Figure 37:
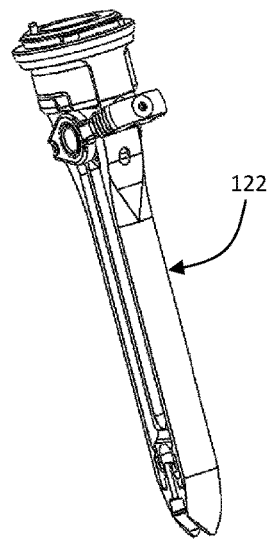
FIG. 37 is perspective view of a partially disassembled cerclage inserter instrument for cleaning purposes.

Depressing button 806 against the biasing spring force moves button wall 809 out of mid groove 720 thus permitting lock driver 702 to be retracted out of drive pocket 408 of lock cap 400 typically by manual distraction on finger wheel 714. Similarly, bias button 806 may be used to disassemble cerclage inserter 108 such that individual components can be cleaned. For example, control portion 900 may be removed, then bias button 806 depressed for removal of lock driver 702 as illustrated in FIG. 37. Upon removal of lock driver 702, other components such as provisional lock cap driver portion 800A may also be removed for cleaning.

FIG. 27 illustrates an exploded view of a preferred embodiment of cerclage inserter 108 including a control portion 900 and internal components. Control portion 900 comprises control handle 902 formed from control body 901 and is further illustrated in FIGS. 33-36. Grip surface 903 is available to the user to grip and control cerclage inserter instrument 108. One or more grip apertures 914 extend through grip surface 903 to provide additional user grip friction when handling instrument, reduce weight, to access components located inside control handle 902, and for cleaning access. One or more grip grooves 920 may also extend in control body for gripping purposes and weight reduction. End pocket walls 933 radially define an open end pocket 917 at proximal end of control handle 902. Floor 934 is generally perpendicular to axis-M and divides end pocket 917 from distal pockets 928 and 922. Extending proximally along axis-M from floor 934 is drive shaft 918 terminating with tensioner platform 915 for abutting a tensioner device and wherein drive shaft 918 is further defined by radially placed drive faces 919 here in the form of a hex which may be used to impart rotation during assembly of components. Inside control body 901 and extending generally parallel to axis M is inter-pocket wall 927 defining boundary of control pocket 928 and secondary bevel gear pocket 922. Gear pocket wall 929 also defines pocket 922. Inner gear shaft face 924 formed in inner-pocket wall 927 and outer gearshaft face 925 formed in gear pocket wall 929 define gearshaft aperture 923. Control aperture 916 is sized to pass a surgical cable 502 as are other central axis apertures defined earlier such that cable may be extended through instrument 108 to cable fixation device 100.

Primary bevel gear 909 and secondary bevel gear 910 cooperate to transit forces applied by a user through a torsion wrench 935 to rotate lock driver 702 and advance lock cap 400. Torsion wrench 935 comprises a wrench handle 936 for grasping by a user and a wrench drive 937, such as a hex for example, configured to transmit forces through complementing inner coupler drive faces 938 to outer coupler drive faces 943 of drive coupler 912 to secondary drive face 945 on secondary bevel gear 910. As illustrated in the section view of FIG. 27D, drive coupler 912 comprises an extended coupler boss 939 with coupler groove 940 configured to seat secondary bevel clip 913 therein. Coupler taper 942 may be used to assist entry of wrench drive 937 and snap groove 941 may be used to prevent unintended release of torsion wrench 935. Coupler 912 resides in gearshaft aperture 923 and extends through secondary bevel gear 910 which is housed within secondary bevel gear pocket 922 and held in position by coupler rim 944 and secondary bevel clip 913 of drive coupler 912.

Figure 27B:
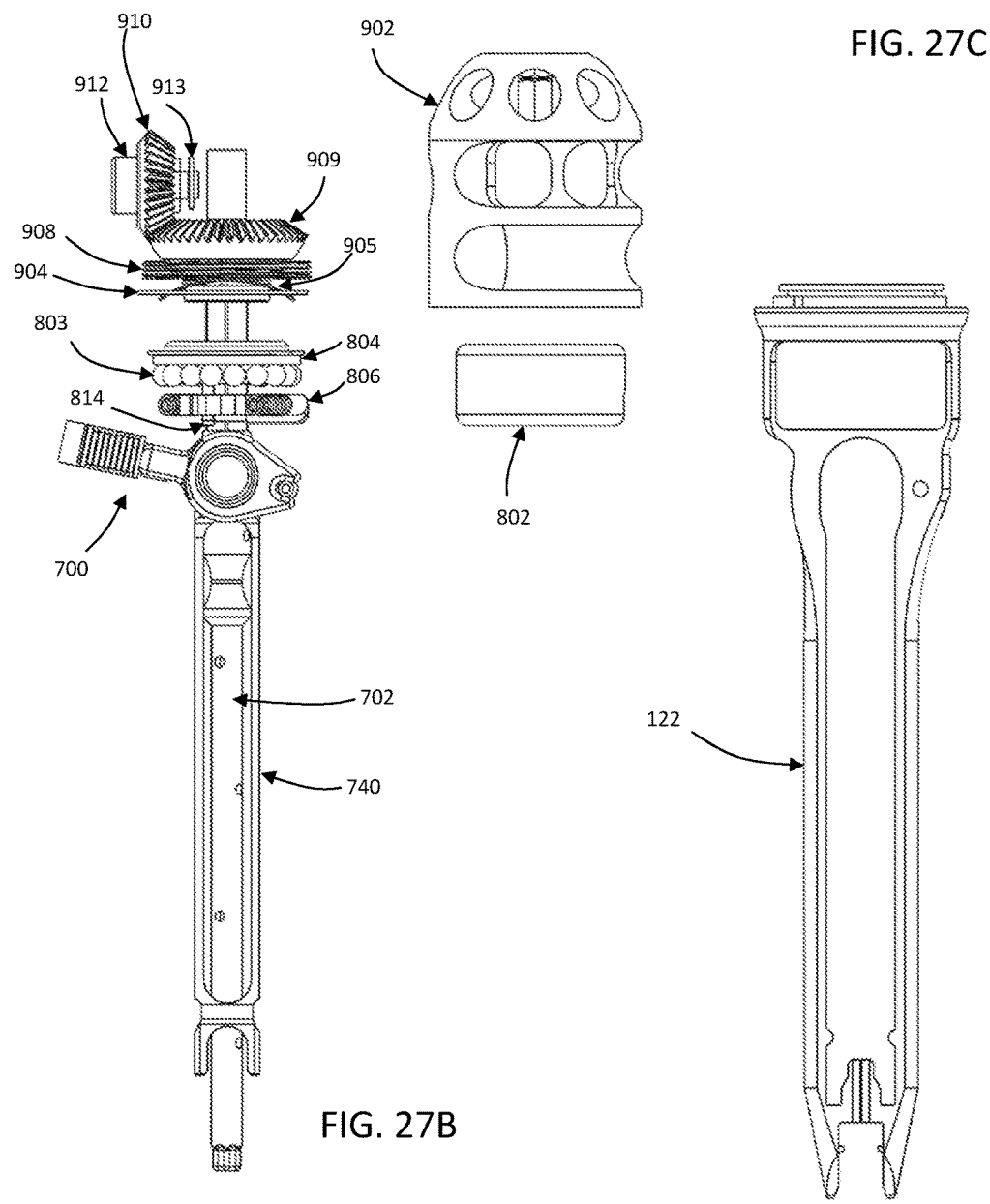
FIG. 27B is a side view of the cerclage inserter of FIG. 27 with internal components exposed by displacement of outer components.

Primary bevel gear 909 comprises primary drive faces 946 configured to complement and rotably engage first crank faces 724 of lock driver 702 and wherein lock driver 702 is free to slide against drive faces 946 relative to axis G. FIG. 27B illustrates internal components of cerclage inserter 108 with components 902, 802, and 122 displaced to the side. Primary bevel gear 909 is housed distally within control pocket 928 rotating above proximal bearing 906 and proximal race 908.

Control restraint clip 904 spans spring groove 182 on frame body 122 and control groove 926 to releasably secure control portion 900 to frame body 122. Wave spring 905 tightens gaps between interfacing components. Proximal bearings 906 are partially disposed in proximal race 908. The outer perimeter of proximal race 908 comprises race threads 931 to complement handle threads 921 of control handle 902 for threaded engagement therebetween. Proximal race 908 comprises a plurality of race holes 932 in which proximal bearing 906 is housed. Race pin 911 extends from race pin hole 184 through one of race holes 932 to maintain threaded position of proximal race 908 after fully threaded into control handle 902. Control restraint ring 907 maintains position of components.

A cable fixation device 100 will preferably be packaged pre-assembled with collet 300 loosely seated within compression walls 204 and lock cap 400 loosely threaded within fixation wall 202. A cable drum 501 is pre-seated within head walls 205. A surgical kit may be provided for use in the surgical suite comprising the cable fixation device, a cerclage inserter, a cable passer, and a cable tensioner.

Figure 39:
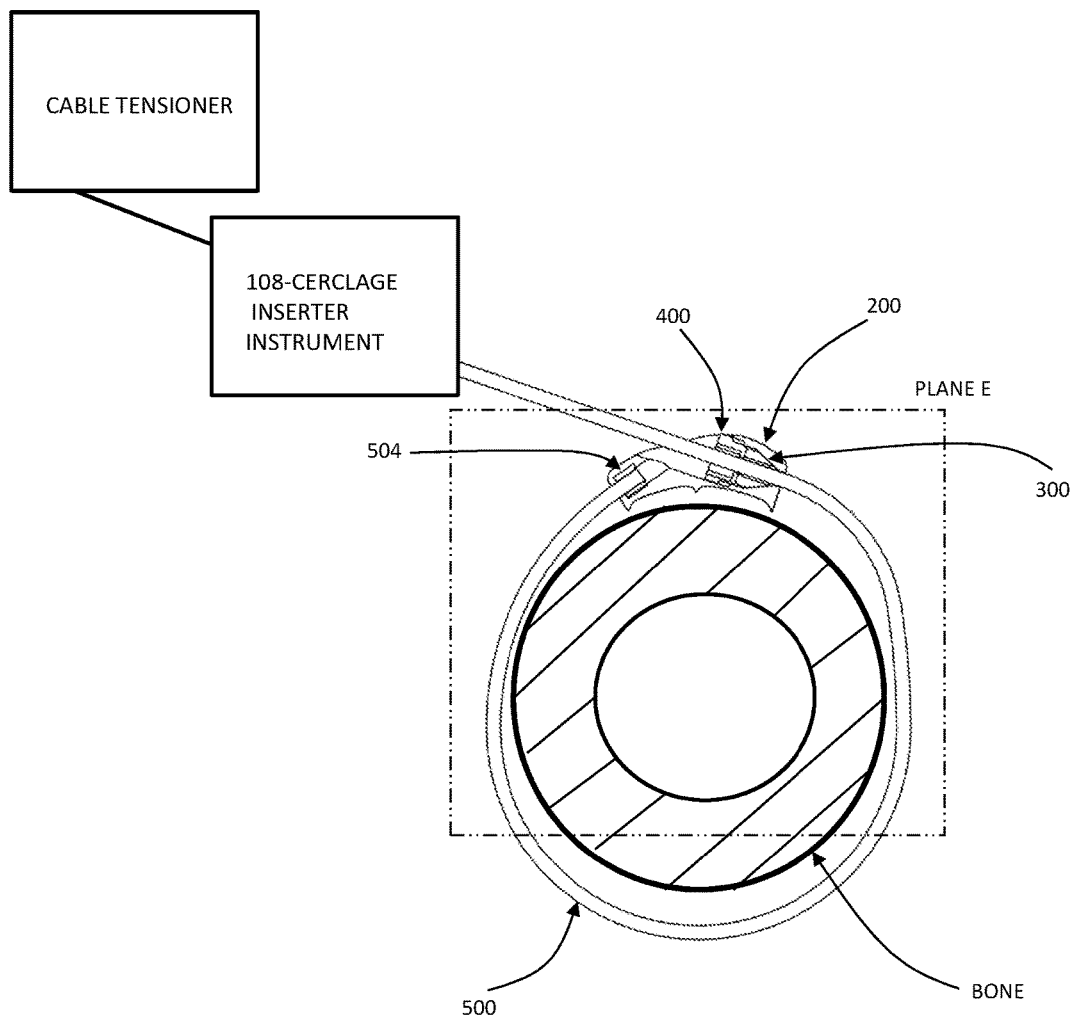
FIG. 39 is a cross-sectional view through plane E of a surgical cable cerclage encircling a long bone, passing through a fixation assembly in preparation for tensioning by a cable tensioner and fixation by action of a cerclage inserter instrument.

In one embodiment, a surgical method for utilizing a cable fixation device 100 begins with the step of passing a free end of a surgical cable though an incision and around a bone or bone segments to be stabilized (FIG. 39). A surgical cable passer known in the art (not shown) may be utilized for this purpose. The passer typically comprises a passer handle connected to a passer shaft for guiding a semi-circular passer tube around the outer surface of the bone. A surgical cable is fed into the passer tube until exposed out the other side. The passer may then be removed leaving surgical cable encircled around the bone.

The user activates clasp activator 700 assuring ram is distracted proximally causing ram 740 to deflect frame legs 132 outward causing a consequent widening of clamp window 126. Control slots 230 on cable fixation device 100 are then aligned with restraint ribs 130 within clamp window 126 of cerclage inserter 108. Clamp housing 200 is moved generally perpendicular within clamp window 126 until restraint ribs 130 seat in control slots 230 wherein driver head 706 is aligned with drive pocket 408. The user activates clasp activator 700 by moving lever handle 772 distally causing ram 740 to also move distally. Ram horns 758 pinch sides of pod 148 together resulting in a consequent narrowing of clamp window 126 therein firmly holding clamp housing 200 therebetween opposing arm faces 128.

The user then advances distally by hand lock driver 702 wherein driver head 706 occupies drive pocket 408 of lock cap 400. Button 806 may move against lock driver rod 702 causing it to be restrained from axial movement.

A lead 506 of cable 500 is then fed through inlet wall 206 of clamp housing 200, through a central aperture 306 of collet 300, through a cable wall 402 of lock cap 400 and through inner cannula 712 of lock driver 702. The surgeon may continue to thread cable lead 506 into a surgical cable tensioning device. Alternatively, the surgeon may immediately apply a provisional tension on cable 500 by hand and provisionally fix cable 500 within fixation assembly 102 by finger advancing thumb cup 802 by hand until lock cap 400 is sufficiently snug thereby retaining cable tension in cerclage 500.

For final tensioning and locking, a surgical cable tensioner (common in the prior art) may be used. Cable lead 506 is threaded into the cable tensioner until all cable slack is removed and cable tensioner abuts tensioner platform 915 on control handle 902. The cable is restrained in the cable tensioner and thumb cup or wheel 802 is advanced in an opposite direction by hand until lock cap 400 is loosened thereby freeing cable 500 in cerclage to be retensioned. The surgeon then tensions the cable to a predetermined level using the tensioner.

The surgeon then uses a torsion wrench 935 to advance drive coupler 912 causing consequent rotation of secondary bevel gear 910 and primary bevel gear 909 which causes consequent rotational advancement of lock driver 702. This causes lock cap 400 to advance and restrain cable 500 at desired tension within tightened collet 300. This process of loosening lock cap, retensioning, then retightening lock cap may be repeated without damage to the surgical cable.

The user then retracts lock driver 702 proximally to remove driver head 706 from drive pocket 408 which may require simultaneous depression of button 806. The user again activates clasp activator 700 assuring ram 740 is distracted proximally causing ram 740 to deflect frame legs 132 outward causing a consequent widening of clamp window 126. Cerclage inserter instrument 108 is moved in a direction generally parallel to control slots 230 thereby causing release of clamp housing 200 from instrument 108. The cerclage inserter instrument 108 is then retracted proximally and removed from the surgical site. Wound closure may ensue.

In an alternative method, portions of the cable fixation device 100 may be assembled during surgery. In preferred embodiments head of cable 502 is configured in size to be passable through the cable passer then assembled with clamp housing 200 after the passer instrument is removed. This feature provides for the cable 502 to be passed in either direction through the passer tube. In cases where introducing the passer instrument from one side of the bone is easier than the other, the surgeon may be forced with prior art systems to introduce the passer from the more difficult side to assure clamp housing 200 is positioned in a convenient direction for tensioning and locking. This assembled in surgery feature ensures the surgeon will be able to enjoy the convenience of introducing the passer instrument around the bone from either entry position while also being assured the clamp housing will be directed in a convenient direction for tensioning and locking. Assembly in preferred embodiments is completed by passing the cable around the bone then dropping cable 502 through cable slot 213. Cable 502 is pulled until cable drum 501 is seated in head aperture 212 and against head stop surface 1220. This assembly during surgery feature is made possible by cable slot 213 as it provides a path for cable drum 501 to be seated in head aperture 212 without requiring cable lead 506 to pass through head aperture 212 first.

The foregoing invention has been described in accordance with the relevant legal standards, thus the description is exemplary rather than limiting in nature. Variations and modifications to the disclosed embodiment may become apparent to those skilled in the art and fall within the scope of the invention.

The invention claimed is:

1. A surgical cable fixation kit comprising:
   an implantable cable;
   a clamp housing;
   a lock cap for advancement into said clamp housing for locking said implantable cable;
   a multipart collet compressible about said cable;
   said multipart collet comprising a plurality of collet sections;
   a cerclage inserter instrument;
   a torsion wrench;
   said cerclage inserter instrument comprising a bevel gear pair for transferring forces from said torsion wrench;
   a lock driver;
   said lock driver comprising an inner cannula sized to pass said implantable cable therethrough;
   and a pair of deflectable frame legs for clasping on said clamp housing.

2. The surgical cable fixation kit of claim 1 further comprising surfaces between said lock cap and said multipart collet that slide relative to each other for minimizing twisting of said cable when advancing said lock cap.

3. The surgical cable fixation kit of claim 1 further comprising oblique angled lock walls extending from opposed ends of said multipart collet for compressing said multipart collet about said implantable cable during locking.

4. A cable fixation device for securing bone segments comprising:
   a clamp housing;
   a surgical cable;
   said surgical cable having a cable head;
   a head aperture situated within said clamp housing for securing said cable head within said head aperture;
   a lock aperture within said clamp housing;
   a multipart collet housed within said lock aperture;
   said multipart collet comprising a plurality of individual collet sections encircling said surgical cable;
   a lock cap housed within said lock aperture;
   said surgical cable formed into a cable loop with a portion of said cable residing within said multipart collet;
   wherein said head aperture and said lock aperture intersect and are contiguous;
   and wherein the cable fixation device comprises one or more of: a) said multipart collet having a first lock wall and a second lock wall extending from opposed ends of said multipart collet for compressing said multipart collet about said surgical cable during locking; and b) said lock cap having a locking cap drive axis and said clamp housing further comprises a pair of opposed control slots wherein the elongate side of each control slot is perpendicular to said locking cap drive axis.

5. The cable fixation device of claim 4 further comprising said cable loop orientated in a single plane.

6. The cable fixation device of claim 4 further comprising an enlarged cable head of said cable and a head stop surface positioned within said head aperture to prevent pull out of said enlarged cable head from within said clamp housing.

7. The cable fixation device of claim 6 wherein said enlarged cable head is in the form of a cable drum.

8. The cable fixation device of claim 4 wherein said clamp housing further comprises a concave bottom surface for seating adjacent to bone.

9. The cable fixation device of claim 8 further comprising a plurality of teeth projecting from said concave bottom surface for seating into bone.

10. The cable fixation device of claim 4 wherein said pair of opposed control slots extend into each opposing side surface of said clamp housing for receiving instrumentation.

11. The cable fixation device of claim 10 wherein said pair of opposed control slots extending into each opposing side surface of said clamp housing are aligned generally perpendicular to an elongate axis of said lock aperture.

12. The cable fixation device of claim 4 wherein said multipart collet comprises two individual collet sections.

13. The cable fixation device of claim 4 wherein each collet section is tapered on opposed ends of said collet facilitating well distributed clamping pressure on said surgical cable.

14. The cable fixation device of claim 4 wherein said lock cap comprises a tapered compression wall for compressing said collet sections towards said surgical cable.

15. The cable fixation device of claim 4 wherein said lock cap comprises an interference boss at a proximal end of said lock cap.

16. The cable fixation device of claim 15 wherein said interference boss engages in a friction fit against a passage wall extending through said clamp housing.

17. The cable fixation device of claim 4 wherein each said collet section comprises a cylindrical head face extending between a tapered first lock wall and a tapered second lock wall.

18. The cable fixation device of claim 4 wherein said lock cap further comprises a plurality of drive leads proximal to a drive pocket for easing engagement of a lock cap instrument with said lock cap.

* * * * *